US012759047B2

(12) United States Patent
Seinberg et al.

(10) Patent No.: US 12,759,047 B2
(45) Date of Patent: Oct. 13, 2026

(54) METAL-BASED CORE NANOPARTICLES, SYNTHESIS AND USE

(71) Applicant: Liis Seinberg, Tallinn (EE)

(72) Inventors: Liis Seinberg, Tallinn (EE); Maria Volokhova, Tallinn (EE)

(73) Assignee: Liis Seinberg, Tallinn (EE)

(*) Notice: Subject to any disclaimer, the term of this patent is extended or adjusted under 35 U.S.C. 154(b) by 1016 days.

(21) Appl. No.: 17/792,822

(22) PCT Filed: Jan. 14, 2020

(86) PCT No.: PCT/EP2020/050837
§ 371 (c)(1),
(2) Date: Jul. 14, 2022

(87) PCT Pub. No.: WO2021/144006
PCT Pub. Date: Jul. 22, 2021

(65) Prior Publication Data

US 2023/0067607 A1 Mar. 2, 2023

(51) Int. Cl.

| | |
|---|---|
| ***A61K 49/18*** | (2006.01) |
| ***A61K 41/00*** | (2020.01) |
| ***B22F 1/054*** | (2022.01) |
| ***B22F 1/102*** | (2022.01) |
| ***B22F 1/16*** | (2022.01) |
| ***B22F 9/24*** | (2006.01) |

(52) U.S. Cl.
CPC ............ *B22F 9/24* (2013.01); *A61K 41/0057* (2013.01); *A61K 49/1824* (2013.01); *B22F 1/054* (2022.01); *B22F 1/102* (2022.01); *B22F 1/16* (2022.01); *B22F 2304/054* (2013.01)

(58) Field of Classification Search
CPC ......... B22F 1/02; B22F 1/054; A61K 49/1824
See application file for complete search history.

(56) References Cited

U.S. PATENT DOCUMENTS

| | | | |
|---|---|---|---|
| 8,784,895 | B2 | 7/2014 | Messersmith et al. |
| 2008/0213189 | A1 | 9/2008 | Lee et al. |
| 2018/0297857 | A1 | 10/2018 | Hegmann et al. |
| 2019/0375004 | A1 | 12/2019 | Yamamoto et al. |

FOREIGN PATENT DOCUMENTS

| | | | |
|---|---|---|---|
| CN | 109045309 | A | 12/2018 |
| CN | 109646687 | A | 4/2019 |
| GR | 1008081 | B | 1/2014 |
| JP | 2012513963 | A | 6/2012 |
| WO | 2008096280 | A1 | 8/2008 |
| WO | 2010076237 | A2 | 7/2010 |
| WO | 2010096828 | A1 | 8/2010 |

OTHER PUBLICATIONS

Wei et al. "Compact zwitterion-coated iron oxide nanoparticles for in vitro and in vivo imaging", Integr. Biol., 2013, 5, 108-114 (Year: 2013).*

Nam et al. "Single-Crystalline Hollow Face-Centered-Cubic Cobalt Nanoparticles from Solid Face-Centered-Cubic Cobalt Oxide Nanoparticles", Angew. Chem. Int. Ed. 2008, 47, 9504-9508 (Year: 2008).*

Zhang et al. "Monodispersity control in the synthesis of monometallic and bimetallic quasi-spherical gold and silver", | Nanoscale, 2010, 2, 1962-1975 (Year: 2010).*

"International Search Report and Written Opinion on Aug. 17, 2020 in corresponding International Application No. PCT/EP2020/050837."

Huang, et al.,"Effects of Nanoparticle Size on Cellular Uptake and Liver MRI with PVP-Coated Iron Oxide Nanoparticles", ACS Nano. Dec. 28, 2010; 4(12): 7151-7160. doi:10.1021/nn101643u.

Kohara, et al., "Carboxylated SiO2-coated a-Fe nanoparticles: towards a versatile platform for biomedical applications", Chem. Commun., 2013, 49, 2563-2565.

Yamamoto, et al., "Transformation of Nano- to Mesosized Iron Oxide Cores to r-Fe within Organic Shells Preserved Intact", Chem. Mater. 2011, 23, 1564-1569. dx.doi.org/10.1021/cm103412h.

Dey, "Dopamine Loaded SiO2 Coated Fe3O4 Magnetic Nanoparticles: A New Anticancer Agent in pH-Dependent Drug Delivery", ChemistrySelect, , 4, p. 12190, 2019.

* cited by examiner

*Primary Examiner* — James W Rogers
(74) *Attorney, Agent, or Firm* — ALG Intellectual Property, LLC

(57) ABSTRACT

A nanoparticle includes a metal-based core, a first coating layer substantially covering the metal-based core to generate a coated metal-based core, and a second coating layer at least partially covering the coated metal-based core, wherein the metal-based core comprises at least one transition metal, and wherein the metal-based core comprises the at least one transition metal substantially in a state of zero oxidation.

7 Claims, 10 Drawing Sheets

| Fe@$SiO_2$ (cubic) | |
|---|---|
| $M_s$ | 181 emu/g-Fe |
| $H_c$ | 0,02 T |

METAL-BASED CORE NANOPARTICLES, SYNTHESIS AND USE

The invention lies in the field of nanostructures and particularly in the field of nanoparticles. The invention relates to the synthesis of metal-based core nanoparticles and more particularly, the present invention relates to metal-based core nanoparticles, a method for synthesizing such nanoparticles, a method comprising using such nanoparticles.

Nanotechnology is field of research bearing a plurality of challenges and fast development since last century comprises studying, designing, creating, synthesizing, manipulating and applying of materials, apparatus and functional systems through the control of matter at the nanoscale as well as exploitation of phenomena and properties of nanomaterials. When matter is manipulated at such a tiny scale, it may present entirely properties, which nanotechnology may use to create novel materials as well as devices and systems with unique properties. Thus, great avocation has been dedicated to studying physical, chemical and biological phenomena occurring at nanometric scale. Nowadays, there are many method, instruments, devices and techniques of nanometric dimensions with sufficient precision that may facilitate exploiting nanomaterials.

Furthermore, nanotechnology comprises engineering functional system on a nano scale, which may comprise more advanced concepts and which final aim may be to build materials, systems and methods from a smaller to a larger scale, using and/or exploiting properties of materials and/or systems at a nanometric scale.

Materials at nano scale may comprise a wide class of materials, which may include for instance nanoparticles. Moreover, nanoparticles may also comprise particulate substances, which depending on the overall geometry, which also comprises 1D, 2D or even 3D materials. In general terms, nanoparticles are particles existing on a nanometer scale, typical 100 nm or below in at least one dimension. Nanoparticles are versatile particles, as they possess special properties, for instance, physical properties such as uniformity, conductance, or optical properties, that make allow them diverse applications in a plurality of discipline, for instance, fields related to materials science, biology and/or medicine. In other words, nanoparticles may be of particular interest, as they may influence physicochemical properties of substances, which may potentially be of interested, for example, in medical applications.

However, nanoparticles are not simple materials, but in general, nanoparticles may comprise rather complex substances and/or systems. Therefore, nanoparticle may be categorized in different groups based upon their morphology, dimensions and their physical and/or chemical properties.

Some nanoparticles may principally comprise nanoparticles with metallic precursors, therefore they may also be referred to as metallic nanoparticles or metal nanoparticles. Such nanoparticles may be of particular interest, as they may exhibit unique optical and/or electrical properties. For instance, nanoparticle comprising noble metals such as gold or silver may encounter a plurality of applications, such as application in electromagnetic fields.

Application of metal nanoparticles may face specific challenges, which may occur isolated or as a part of a complex series of properties to be achieved. For example, but not limited to, facet, size and shape-controlled synthesis may be crucial for creating, developing and/or utilizing metal nanoparticles.

There are other several metal nanoparticles that have been center of intense research and development due to their broad usage range in different fields, for example, biomedical fields such as tissue engineering, detection of proteins and magnetic resonance imaging (MRI) contrast enhancement. Some of these application fields may require even more specific nanoparticle features, for example, for biomedical applications it may be critical to know properties of synthesized nanoparticles with particular size control, and all that without jeopardizing viability of production such as yield of synthesis method. Size of nanoparticles is of particular interest as nanoparticles with a same nature but different sizes may act differently in different systems, e.g. in human organism for biomedical applications.

U.S. Pat. No. 8,784,895 B2 relates to nanoparticles including a metallic core having a length along each axis of from 1 to 100 nanometers and a coating disposed on at least part of the surface of the metallic core, wherein the coating comprises polydopamine, along with methods for making and using such nanoparticles.

CN 109646687 A to an iron-based T weighted magnetic resonance imaging contrast agent and a preparation method thereof. Synthesis of an iron-based T weighted magnetic resonance imaging contrast agent is detailed. The obtained iron-based T weighted magnetic resonance imaging contrast agent has a better contrast enhancement ability, has good water dispersibility and more easily reaches each tissue organ through blood circulation.

CN 109045309 A relates to an iron-based T1 weighted magnetic resonance imaging contrast agent and a preparation method thereof, and belongs to the field of contrast agents. The iron-based T1 weighted magnetic resonance imaging contrast agent is prepared by mixing a carbon source, EDTA (Ethylene Diamine Tetra Acetic Acid) and an iron source with water, heating and reacting to obtain a transparent reddish-brown solution. The carbon source is selected from at least one of glutathione, citric acid and cysteine. The iron source is selected from at least one of soluble iron salts and soluble ferrous salts. The iron-based T1 weighted magnetic resonance imaging contrast agent, provided by the invention, has the advantages of good biocompatibility, wide application range and capability of being used for T1 weighted magnetic resonance imaging.

US 2018297857 A1 relates to a low temperature, aqueous synthesis of polyhedral iron oxide nanoparticles (IONPs). The modification of the co-precipitation hydrolysis method with Triton X surfactants results in the formation of crystalline polyhedral particles. The particles are herein termed iron oxide “nanobricks” (IONBs), as the varieties of particles made are all variations on a simple “brick-like”, polyhedral shape such as rhombohedral shape or parallelogram as evaluated by TEM. These IONBs can be easily coated with hydrophilic silane ligands, allowing them to be dispersed in aqueous media. The dispersed particles are investigated for potential applications as hyperthermia and T2 MRI contrast agents.

GR 1008081 B relates to a general approach where magnetic-field directed nanoparticle assembly affords water-dispersible ferrimagnetic colloidal nanoclusters (CNCs) with low cytotoxicity and raised intra-aggregate magnetic material volume fraction. Their unique magneto-structural characteristics, a consequence of the oriented attachment and crystallographic alignment of the individual superparamagnetic iron-oxide nanocrystals out of which they are composed, together with their single-phase chemical nature (maghemite) give a much-improved nuclear magnetic relaxation responsiveness against other contrast enhancing agents. The transverse r2 relaxivity is found enhanced by a factor of at least 4 with respect to the commercial product Endorem, over a broad frequency range (1-200 MHz). We claim an alternative, cost-efficient pathway for the production of novel nanoarchitectures for MRI-based diagnostic applications.

WO 2008 096280 A1 refers to method for visualizing biological material, preferably by MRI, comprising the steps of: (i) bringing a population of coated nanoparticles into contact with said biological material, each of which nanoparticles comprises a) a metal oxide of a transition metal, said metal oxide preferably being paramagnetic and preferably comprising a lanthanide (+III) such as gadolinium (+III), and b) a coating covering the surface of the core particle, and (ii) recording the image; wherein the coating is hydrophilic and comprises a silane layer which is located next to the surface of the core particle and comprises one or more different silane groups which each comprises an organic group R and a silane-siloxane linkage where a) R comprises a hydrophilic organic group R' and a hydrophobic spacer B, b) O is oxygen directly binding to a surface metal ion of the metal oxide, and c) C is carbon and is also part of B.

US 2019 0375004 A1 relates to a new, highly magnetically stable magnetic material which has higher saturation magnetization than ferrite-based magnetic materials, and with which problems of eddy current loss and the like can be solved due to higher electric resistivity than that of existing metal-based magnetic materials, and a method for manufacturing the same. A magnetic material powder is obtained by reducing in hydrogen Ni-ferrite nanoparticles obtained by wet synthesis and causing grain growth, while simultaneously causing nano-dispersion of an $\alpha$-(Fe, Ni) phase and an Ni-enriched phase by means of a phase dissociation phenomenon due to disproportional reaction. The powder is sintered to obtain a solid magnetic material.

Huang et al. (ACS Nano. 2010 Dec. 28; 4(12): 7151-7160) relates to the effect of nanoparticular size on cellular uptake and liver magnetic resonance imaging with polyvinylpyrrolidone-coated metal oxide nanoparticles. Furthermore, Huang et al. relates to spherical nanoparticles with different sizes, exhibiting good crystallinity and high T2 relaxivities.

Yamamoto et al. (*Chem. Mater.,* 2011, 23, 1564-1569) refers to nanoparticles of iron-based nanoparticles, which are made corrosion-resistant and dispersible in polar and nonpolar solvents by coating these with inner and outer layers of amorphous silica and organics like poly(ethylene glycol), respectively. Yamamoto et al. further refers to a method to reduce the iron at temperatures low enough to keep the organic layer intact, via using $CaH_2$ as a reductant and a working temperature of 200 to 300° C., where thermal particle adhesion did not take place, formation of impurities like iron silicates was suppressed, and the overall morphological features of the starting particles were preserved.

Kohara et al. (*Chem. Commun.,* 2013, 49, 2563-5) refers to carboxylated $SiO_2$-coated iron nanoparticles prepared via $CaH_2$-mediated reduction of $SiO_2$-coated $Fe_3O_4$ nanoparticles followed by a surface carboxylation. These iron-based nanoparticles possess a large magnetization of 154 emu per g-Fe, enhanced corrosion resistivity, excellent aqueous dispersibility, and low cytotoxicity.

Moreover, medical imaging is used as a common method to diagnose wide range of medical condition. For instance, magnetic resonance imaging (MRI) may be used to visualize soft tissues and organs. Over 60 million MRI scans worldwide are carried out in a year, where 30% of contrast agents are used to increase image quality (J. Wahsner *Chem. Rev.* 2019, 119, 2, 957-1057). Gd-based contrast agents offer still several side effect such as toxicity and it tends to cause nephrogenic systemic fibrosis and reports have confirmed Gd depositing to human brain (J. Wahsner *Chem. Rev.* 2019, 119, 2, 957-1057). Furthermore, some organs are impossible to image without MRI contrast agent such as liver and spleen, which has lead research on nontoxic Gd-free contrast agents such as iron oxide-based contrast agents.

In light of the above, it is therefore an object of the present invention to overcome or at least to alleviated the shortcomings and disadvantages of the prior art. More particularly, it is an object of the present invention to provide metal-based nanoparticles and a method for synthesizing such nanoparticles comprising smaller and well-control dimensions as well as low toxicity functional layer.

These objects are met by the present invention.

In a first aspect, the present invention relates to a nanoparticle comprising a metal-based core, a first coating layer substantially covering the metal-based core to generate a coated metal-based core, and a second coating layer at least partially covering the coated metal-based core, wherein the metal-based core comprises at least one transition metal, and wherein the metal-based core comprises the at least one transition metal substantially in a state of zero oxidation.

In other words, the present invention relates to a nanoparticle comprising a metal-based core, which may comprise a first coating layer and a second coating layer, wherein the first coating layer may be different from the second coating layer, which may in some instances be particularly advantageous, as it may allow to provide a plurality of different characteristics to the nanoparticle. For instance, the first coating layer may comprise a (semi)impermeable layer, which may, for example, hinder the diffusion of, for example, but not limited to, compounds, radicals, electrons, which may alter and/or deteriorate the metal-based core. Therefore, the first coating layer comprise a layer that may reduce, hinder or eliminate the diffusion, for example, or oxygen, which may allow the metal-based core of the nanoparticle to remain substantially in a state of zero oxidation. Such a layer may also be advantageous, as it may on the one hand protect the metal-based core from oxidation, and consequently, the nanoparticle may be less prone to undergo aggressive processes, such as corrosion. Moreover, hindering the occurrence the oxidation-reduction reactions may also facilitate lessen the dissolution of the metal-based core, which may as well contribute to reducing the release of metallic ions to a medium surrounding the nanoparticle. Such a reduced released of metallic ions may be particularly advantageous, as it may allow to reduce the toxicity of the nanoparticle in, for example, a biological environment.

Furthermore, the second coating layer may be particularly advantageous, as it may allow to tune properties of the nanoparticle, which may encounter specific applications. For instance, the second coating layer may render the nanoparticle soluble in water or at least may increase it hydrophilic, which may be beneficial, as it may allow and/or facilitate to dissolve and/or disperse the nanoparticles in an aqueous medium. Increasing the hydrophilicity of the nanoparticle may further allow to utilize the nanoparticle in a plurality of water-containing system, such as, but not limited to, systems comprising isotonic solutions, complex oil-water-containing systems wherein the water fraction may disperse the nanoparticles in the system, which may allow applications in, for example, interface-depend process such as the application of dermatological pharmaceutical compositions. Similarly, the second coating layer may also make the nanoparticle soluble and/or dispersible in an organic solvent, e.g. an oil, which would allow the nanoparticle to be dissolved and/or disperse in the oil fraction of the previous example.

The at least one transition metal may comprise at least one transition metal selected from a group consisting of Fe, Co, and Ni.

The at least one transition metal may comprise at least one transition metal selected from a group consisting of Cu, Au, Ag, Pd, Pt, Mn, Gd, Tb, Dy, Ho, Er, Tm and Cf.

The first coating layer may comprise a siloxane-based layer as represented in formula 1

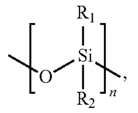

wherein n may be an integer greater than or equal to 1 and less than or equal to 15, and $R_1$ and $R_2$ may be each a moiety that may be independently selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 15, and —COX wherein X may be one of F, Cl, Br, and I.

The integer n in Formula 1 may be preferably between 1 to 10.

The integer n in Formula 1 may be preferably between 1 to 5.

The first coating layer may comprise an inner terminal portion and an outer terminal portion, wherein the inner terminal portion defines an inner surface and the outer terminal portion defines an outer surface of the first coating layer.

The second coating layer may comprise an inner terminal portion and an outer terminal portion, wherein the inner terminal portion defines an inner surface and the outer terminal portion defines an outer surface of the second coating layer.

The second coating layer may comprise a compound comprising at least one moiety.

The at least one moiety may be arranged at the outer terminal portion of the second coating layer.

The at least one moiety may be a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 15, and —COX wherein X may be one of F, Cl, Br, and I.

The at least one moiety may comprise at least one compound represented in formula 2

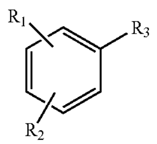

wherein $R_1$, and $R_2$ each and independently may be selected from a group consisting of —OH, —COOH, —$NH_2$, —SH, —$CONH_2$, —OX, and —COX wherein X may be a halogen selected from a group consisting of F, Cl, Br, and I, and wherein $R_3$ may be independent of $R_1$ and $R_2$ a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 20, and —COX wherein X may be one of F, Cl, Br, and I.

At least one of $R_1$ and $R_2$ in the compound represented by Formula 2 forms a chemical bond connecting the compound represented in formula 2 to the first coating layer.

The at least one moiety may comprise at least one compound selected from a group consisting of a (poly) zwitterionic, and an alkoxysilane.

The second coating may be functionalized with at least one functional group.

The functional group derived from at least one compound selected from a group consisting of an epoxide, an organo-siloxane, an epoxy-siloxane, an amino alkyl alkoxysilane, and a tetra alkyl di-siloxane.

The functional group derived from at least one compound selected from a group consisting of a (poly)peptide, wherein the (poly)peptide may comprise at least one peptide with a molecular weight between 1 and 100 kDa, preferably between 10 and 50 kDa, such as between 20 and 40 kDa, and a (poly)saccharide, wherein the (poly)saccharide may comprise at least one saccharide with a molecular weight between 100 and 2000 kDa, preferably between 200 and 1500 KDa, such as between 300 and 1200 kDa, such as between 400 and 1000 kDa.

The (poly)saccharide may be at least one of dextran, chitosan, glycogen, cellulose, and alginate.

The functional group further may comprise at least one of DNA, and RNA.

The functional group further may comprise at least one analgesic compound.

The functional group further may comprise at least one of antibody, wherein the at least one antibody may be for identifying lesions in tissues via antibody-binding.

The lesions may be brain lesions.

The chemical bond may be a covalent bond.

The chemical bond may be a non-covalent bond.

The first coating layer may comprise an inner surface and an outer surface.

The inner surface of the first coating layer may be chemically bond to metal-based core.

The nanoparticle may comprise a cubic crystal structure.

The nanoparticle may comprise at least one crystal structure of tetragonal, orthorhombic, hexagonal, trigonal, monoclinic, triclinic, and primitive.

The crystal structure may comprise an edge length between 1 and 100 nm.

This may be beneficial, as nanoparticles with a same nature but different size may behave and/or play a different role in different system, e.g. in organisms. For instance, smaller nanoparticles, such as nanoparticles of up to 25 nm in diameter, may yield brighter contrast in MRI measurements than bigger nanoparticles. However, smaller nanoparticle may exhibit a tendency to deposit on organs. Therefore, the nanoparticles of the present invention may be particularly advantageous, as they are conferred with properties that may allow them to hinder deposition on organs.

The edge length of the crystal structure may be between 5 and 80 nm, preferably between 8 and 70 nm, such as between 10 and 60, such as between 15 and 50m, such as 20 and 40 nm.

The crystal structure of the nanoparticle may comprise at least one lattice type of a body-centered, a face-centered, and side centered.

In one embodiment, the nanoparticle may comprise a spherical structure with a diameter between 5 and 80 nm, preferably between 8 and 70 nm, such as between 10 and 60, such as between 15 and 50m, such as 20 and 40 nm.

The nanoparticle exhibits a saturation magnetization ($M_s$) in the range of 40 to 218 emu per g-M.

This may be advantageous, in particular for applications such as magnetic resonance imaging. From the perspective of magnetic resonance imaging (MRI), a high saturation magnetization ($M_s$) values may be crucial for MRI signal enhancement since contrast agents with high $M_s$ may increase transverse relaxation rates ($1/T_2$) of proton spins ($1/T_2$), $\propto M_s^2$)

The nanoparticle exhibits a coercivity ($H_c$) lower than 0.050 T, preferably lower than 0.010 T, such as 0.019 T.

The nanoparticle may be a ferromagnetic nanoparticle.

The nanoparticle may be a ferrimagnetic nanoparticle.

The nanoparticle may be water soluble.

The first coating layer covers at least 80% of a surface of the metal-based core, preferably at least 90%, more preferably at least 99%.

The nanoparticle covered with the first coating layer exhibits a saturation magnetization ($M_s$) higher than 45 emu/g-M, preferably higher than 70 emu/g-M, more preferably higher than 100 emu/g-M, such as higher than 150 emu/g-M, such as higher than 180 emu/g-M, such higher than 200 emu/g-M, such as higher than 220 emu/g-M.

The second coating layer covers at least 25% of the outer surface of the first coating layer, preferably at least 40%, more preferably at least 50%.

The second coating layer covers 90% or less, preferably 80% or less, more preferably 70% or less of the outer surface of the first coating.

The nanoparticle may be water and exhibits a polydispersity index (PDI) lower than 0.7, preferably lower than 0.6, more preferably lower than 0.5, such as lower than 0.4, such as lower than 0.3, such as lower than 0.2, such as lower than 0.1.

The nanoparticle may be suitable for magnetic resonance imaging.

The nanoparticle may be for use as a soft or field excited magnets.

In one embodiment, the soft field may be between 1 T and 20 T, preferably between 1.2 T and 15 T, more preferably between 1.5 T and 10 T.

The nanoparticle may be for use in drug delivery.

The nanoparticle may be for use as medicament.

In a second aspect, the present invention relates to a method for synthesizing a nanoparticle, the method comprising the steps of: (i) preparing a metal oxide nanoparticle comprising a metal oxide with a chemical structure represented as $M_nO_mbH_2O$, wherein M is a transition metal, n is an integer between 1 and 5, m is an integer between 1 and 10, and b is an integer between 0 and 20, (ii) coating the metal oxide nanoparticle with a first coating layer substantially covering the metal oxide nanoparticle with a layer comprising a first compound to generate a coated metal oxide nanoparticle, (iii) reducing the coated metal oxide nanoparticle with a suitable reducing agent, wherein the reducing agent causes the metal oxide of the coated metal oxide nanoparticle to reduce substantially to a state of zero oxidation to generate a coated metal-based core nanoparticle, and (iv) coating the coated metal-based core nanoparticle with a second coating layer at least partially covering the coated metal-based core nanoparticle with a compound comprising at least one moiety to obtain a double-coated metal-based core nanoparticle.

This approach may be particularly advantageous, as it may allow to coated the metal-based core with a first coating layer and subsequently reduce the metal-based core with affecting the first coating layer, as it may be possible to select the first coating layer with properties such that may withstand a reducing process. Moreover, this may allow to apply a second coating layer comprising a moiety with, for instance, different properties than that of the first coating layer, and additionally or alternatively, the second coating layer may also remain intact, i.e. since the second coating layer is not exposed the conditions of the reducing step, it possible to select moieties with specific properties, that normally, may be alter and/or destroy by reducing agents. This is beneficial, for instance, in case that the second coating layer may comprise a functional group that the prone to be reduced, e.g. a carboxylic group.

The method may comprise washing a plurality of times a product obtained in at least one of the steps (i), (ii), (iii) and (iv) with a suitable washing solution.

In step (i) the method may comprise preparing the metal oxide nanoparticle via using as a precursor a transition metal salt.

The transition metal salt may comprise a n-hydrate nitrate salt, such as a nonahydrate nitrate salt.

In step (i) the transition metal may be one selected from a group consisting of Fe, Co, and Ni.

In step (i) the transition metal may be one selected from a group consisting of Cu, Au, Ag, Pd, Pt, Mn, Gd, Tb, Dy, Ho, Er, Tm and Cf.

In step (i) the metal oxide nanoparticle may comprise a cubic crystal structure.

In step (i) the metal oxide nanoparticle may comprise at least one crystal structure of tetragonal, orthorhombic, hexagonal, trigonal, monoclinic, triclinic, and primitive.

The crystal structure may comprise a size with an edge length between 1 and 100 nm.

The edge length of the crystal structure may be between 5 and 80 nm, preferably between 8 and 70 nm, such as between 10 and 60, such as between 15 and 50m, such as 20 and 40 nm.

In one embodiment, in step (i) the metal oxide nanoparticle may comprise a spherical crystal structure with a diameter between 5 and 80 nm, preferably between 8 and 70 nm, such as between 10 and 60, such as between 15 and 50m, such as 20 and 40 nm.

In step (i) the method may comprise preparing the metal oxide nanoparticle via one-pot pyrolysis.

In step (i) the method may comprise preparing the metal oxide nanoparticle via solvothermal synthesis.

Preparing the metal oxide may comprise a synthesis temperature in the range of 50 to 800° C., preferably between 80 and 500° C., more preferably between 100 and 200° C.

Preparing the metal oxide may comprise a synthesis pressure lower than 10 MPa, preferably lower than 5 MPa, more preferably lower than 1 MPa, such as lower than 0.8 MPa, such as lower than 0.6 MPa, such as 0.1 MPa.

In step (i) the method may comprise controlling the size of the metal oxide nanoparticles via addition of at least one size-controlling agent comprising at least one compound with a molecular weight between 1 and 100 kDa, preferably between 5 and 80 kDa, more preferably between 10 and 40 kDa.

The size-controlling agent may comprise at least one of polyvinylpyrrolidone (PVP), polyethylene glycol (PEG), acetyl acetate, and a surfactant oleic acid.

Step (i) may be performed in a reaction medium comprising at least one compound comprising at least one of N, N-dimethylformamide (DMF), dimethyl sulfoxide (DMSO), ethanol, and water.

In step (ii) the silane-based compound may comprise a compound represented in formula

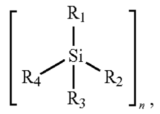

wherein n may be an integer greater than or equal to 0 and less than or equal to 20, and $R_1$, $R_2$, $R_3$, and $R_4$ may comprise each and independently at least one moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 20, and —COX wherein X may be one of F, Cl, Br, and I.

In step (iii) the suitable reducing agent comprising at least one of $CaH_2$, NaH, LiH, $LiAlH_4$, $Mn^{2+}$, Mg or $H_2$ gas, a metal from AI and/or AII group, and a halogen from V II group.

In step (iv) the at least one hydrophilic moiety may comprise a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 15, and —COX wherein X may be one of F, Cl, Br, and I.

In step (iv) the at least one moiety may comprise at least one compound represented in Formula 2

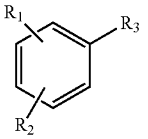

wherein $R_1$, and $R_2$ may comprise each and independently at least one moiety selected from a group consisting of —OH, —COOH, —$NH_2$, —SH, —$CONH_2$, —OX, and —COX, wherein X may be a halogen selected from a group consisting of F, Cl, Br, and I, and wherein $R_3$ may comprise independently from $R_1$ and $R_2$ at least one moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R may be $C_nH_{2n}$ wherein n may be an integer greater than or equal to 0 and less than or equal to 15, and —COX wherein X may be one of F, Cl, Br, and I.

The method may comprise linking the compound represented in formula 2 to the first coating layer comprising the compound represented in Formula 3 via at least one of $R_1$ and $R_2$ of the compound represented in Formula 2.

The second-coated metal-based core nanoparticle may comprise a cubic crystal structure with an edge length between 1 and 100 nm.

The edge length of the cubic crystal structure may be between 5 and 80 nm, preferably between 10 and 60 nm, such as 15 nm.

In one embodiment, one or more of the at least one size-controlling compound may be a dispersant.

In step (i) the method may comprise controlling the size of the metal oxide nanoparticle via controlling the controlling a stoichiometric ratio of at least one of: the metal oxide, and the size-controlling agent.

The stoichiometric ratio between the size-controlling agent and the metal oxide may be A:B, wherein A may be the size-controlling agent and B may be the metal oxide, wherein the stoichiometric ratio may be in the range of 1:3 to 1:150, preferably between 1:4 to 1:120, more preferably between 1:4 to 1:110, such 1:5 to 1:120, such as 1:5 to 1:110, such as 1:6 to 1:100, such as 1:8 to 1:90, such as 1:10 to 1:50, such as 1:12 to 1:40.

The step of controlling the size of the metal oxide nanoparticle may comprise controlling the synthesis temperature, wherein the synthesis temperature may be between 120 and 220° C., preferably between 140 and 200° C., more preferably between 150 and 190° C., such as 160° C.

In step (ii) the method may comprise reducing the metal oxide nanoparticle, whereby the edge length of the nanoparticle increases in a range lower than 20% of an initial edge length, preferably lower than 10%, more preferably lower than 5% of the initial edge length.

In step (iii) the method may comprise reducing the coated metal oxide with a reduction temperature lower than 1000° C., preferably lower than 800° C., more preferably lower than 500° C.

In step (iii) the method may comprise reducing the coated metal oxide with a reduction pressure lower than $10^{-3}$ Pa, preferably lower than $10^{-4}$ Pa, more preferably lower than $10^{-5}$ Pa, such as lower than $10^{-6}$ Pa.

The method may be suitable for preparing the nanoparticle for use in magnetic resonance imaging.

The method may be suitable for preparing the nanoparticle for use in magnetic separation.

The method may be suitable for preparing the nanoparticle for use in drug delivery.

In a third aspect, the present invention relates to a contrast agent comprising a nanoparticle according to any of the preceding nanoparticle embodiments.

The contrast agent further may comprise a suitable medium for dispersing the nanoparticles, wherein the suitable medium causes the nanoparticle to disperse, thereby forming a contrast agent solution.

The contrast agent may be for use in magnetic resonance imaging.

The use of the contrast agent in magnetic resonance imaging may be for medical treatment.

The contrast agent may be for use in whole-body imagining.

The contrast agent may be for use in organ imaging.

The contrast agent may be for use in characterization of soft tissues.

The contrast agent may be for use in diagnosis of tumors and/or metastasis in liver and/or spleen.

The contrast agent may be for use in brain imaging.

The contrast agent may be for use in brain imaging for tumors

The contrast agent may be for use in brain imaging for Alzheimer's disease.

The contrast agent may be for use in preliminary diagnosis of Parkinson's disease.

The contrast agent may be for use in preliminary diagnosis of Multiple Sclerosis (MS).

In a fourth aspect, the present invention relates to a composition comprising a nanoparticle according to any of the preceding nanoparticle embodiments.

The composition may further be configured to target a targeting group comprising at least one of liver, spleen, kidney, blood, heart and brain cells.

The composition may be configured for use as a contrast agent according to any of the preceding contrast agent embodiments for magnetic resonance imaging.

In a fifth aspect the present invention relates to a pharmaceutical composition comprising a nanoparticle according to any of the preceding nanoparticle embodiments.

The pharmaceutical composition may comprise at least one dispersing agent.

The pharmaceutical composition may comprise at least one excipient.

The pharmaceutical composition may be for use as medicament.

The pharmaceutical composition may be for treatment of liver disease.

The pharmaceutical composition may be for treatment of cancer and/or metastatic cancer.

The pharmaceutical composition may be for treatment of hypothermia.

The pharmaceutical composition may be for photodynamic therapy.

In a sixth aspect, the present invention relates to a method for obtaining a magnetic resonance image, the method comprising administering a contrast agent according to any of the preceding contrast agent embodiments to a subject selected to undergo magnetic resonance imaging, and acquiring a contrast-enhanced magnetic resonance image of the subject.

The step of administering the contrast agent may comprise administering the contrast agent via injection.

The step of administering the contrast agent may comprise administering the contrast agent via an oral administration.

The step of acquiring a contrast-enhanced magnetic resonance image may comprise at least one of a T1-weighted scan, and a T2-weighted scan.

In a seventh aspect, the present invention relates to a method of contrast-enhanced magnetic resonance imaging, wherein the method comprises using the contrast agent according to any of the preceding contrast agent embodiments for generating a magnetic resonance image with an increased relaxivity of a targeting group during a relaxation portion of a magnetic resonance image pulse, wherein the increased relaxivity may be achieved via the nanoparticle comprised in the contrast agent.

The method may comprise executing an image obtaining method according to any of the preceding image obtaining method embodiments.

The method may comprise carrying at least one of a T1-weighted scan, and a T2-weighted scan.

The at least one scan may be carried out at a plurality of different times, wherein the different times may comprise at least one of an initial time $t_0$, at least one subsequent time $t_n$.

The at least one scan at the initial time $t_0$ may be performed before injecting the contrast agent to a subject selected to undergo magnetic resonance imaging.

The at least one scan at the subsequent time $t_n$ may be performed after injecting the contrast agent to the subject selected to undergo magnetic resonance imaging.

The at least one scan at the subsequent time $t_n$ at least one time of: a time $t_1$ carried out after 10 min of the injection of the contrast agent, a time $t_2$ carried out after 50 min of the injection of the contrast agent, a time $t_3$ carried out after 3 h of the injection of the contrast agent, a time $t_4$ carried out after 21 h of the injection of the contrast agent, and a time $t_5$ carried out after 1 week of the injection of the contrast agent.

The at least one scan at the initial time $t_0$ and subsequent time $t_n$ may be for use in medical diagnosis.

In an eight aspect, the present invention relates to a method for treating a medical disease, the method comprising the nanoparticle according to any of the preceding nanoparticle embodiments or the pharmaceutical composition according to any of the preceding pharmaceutical composition embodiments, wherein the method comprises administrating the nanoparticle or pharmaceutical composition to a subject.

The method may comprise a route of administration, wherein the route of administration may comprise at least one of oral, and intravenous.

The method may comprise a target action comprising at least one of topical, enteral, and parenteral.

The parenteral target action may comprise at least one of intradermal, subcutaneous, intramuscular, intraperitoneal, and intravenous.

The method may be for treatment of hypothermia.

The method may be for treatment of liver's diseases.

The method may be for treatment of lung's diseases.

The method may be for treatment of cancer.

The method may be for treatment of Alzheimer's disease.

The method may be for treatment of Multiple Sclerosis.

The method may be for treatment of Parkinson's diseases.

In a ninth aspect, the present invention relates to a use of the contrast agent according to any of the preceding contrast agent embodiment.

The contrast agent may be used for diagnosing Alzheimer's disease.

The contrast agent may be used for diagnosing Parkinson's disease.

The contrast agent may be used for diagnosing strokes.

The contrast agent may be used for diagnosing liver disease.

The contrast agent may be used for diagnosing Multiple Sclerosis (MS).

The present technology is also defined by the following numbered embodiments.

Furthermore, the present invention maybe particularly advantageous, as it may allow to increase the quality of magnetic resonances imagining images, and moreover, it may allow to decrease contrast agent administration doses as well as long-term well-being increase.

Below, nanoparticle embodiments will be discussed. These embodiments are abbreviated by the letter "N" followed by a number. When reference is herein made to a nanoparticle embodiment, those embodiments are meant.

N1. A nanoparticle comprising a metal-based core, a first coating layer substantially covering the metal-based core to generate a coated metal-based core, and a second coating layer at least partially covering the coated metal-based core, wherein the metal-based core comprises at least one transition metal, and wherein the metal-based core comprises the at least one transition metal in a state of zero oxidation.

N2. The nanoparticle according to any of the preceding embodiments, wherein the at least one transition metal comprises at least one transition metal selected from a group consisting of Fe, Co, and Ni.

N3. The nanoparticle according to embodiment N1, wherein the at least one transition metal comprises at least one transition metal selected from a group consisting of Cu, Au, Ag, Pd, Pt, Mn, Gd, Tb, Dy, Ho, Er, Tm and Cf.

N4. The nanoparticle according to any of the preceding embodiments, wherein the first coating layer comprises a siloxane-based layer as represented in formula 1

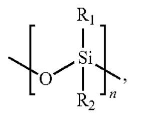

wherein n is an integer greater than or equal to 1 and less than or equal to 15, and $R_1$ and $R_2$ are each a moiety that is independently selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than or equal to 0 and less than or equal to 15, and —COX wherein X is one of F, Cl, Br, and I.

N5. The nanoparticle according to the preceding embodiment, wherein the integer n in Formula 1 is preferably between 1 to 10.

N6. The nanoparticle according to any of the 2 preceding embodiments wherein the integer n in Formula 1 is preferably between 1 to 5.

N7. The nanoparticle according to any of the preceding embodiments, wherein the first coating layer comprises an inner terminal portion and an outer terminal portion, wherein the inner terminal portion defines an inner surface and the outer terminal portion defines an outer surface of the first coating layer.

N8. The nanoparticle according to any of the preceding embodiments, wherein the second coating layer comprises an inner terminal portion and an outer terminal portion, wherein the inner terminal portion defines an inner surface and the outer terminal portion defines an outer surface of the second coating layer.

N9. The nanoparticle according to any of the preceding embodiments, wherein the second coating layer comprises a compound comprising at least one moiety.

N10. The nanoparticle according to the 2 preceding embodiments, wherein the at least one moiety is arranged at the outer terminal portion of the second coating layer.

N11. The nanoparticle according to any of the 2 preceding embodiments, wherein the at least one moiety is a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than or equal to 0 and less than or equal to 15, and —COX wherein X is one of F, Cl, Br, and I.

N12. The nanoparticle according to embodiment N9 or N10, wherein the at least one moiety comprises at least one compound represented in formula 2

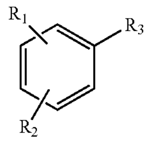

wherein $R_1$, and $R_2$ each and independently are selected from a group consisting of —OH, —COOH, —$NH_2$, —SH, —$CONH_2$, —OX, and —COX wherein X is a halogen selected from a group consisting of F, Cl, Br, and I, and wherein $R_3$ is independent of $R_1$ and $R_2$ a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than or equal to 0 and less than or equal to 20, and —COX wherein X is one of F, Cl, Br, and I.

N13. The nanoparticle according to the preceding embodiment and with features of embodiments N4 to N7, wherein at least one of $R_1$ and $R_2$ in the compound represented by Formula 2 forms a chemical bond connecting the compound represented in formula 2 to the first coating layer.

N14. The nanoparticle according to embodiment N9 or N10, wherein the at least one moiety comprises at least one compound selected from a group consisting of a (poly) zwitterionic, and an alkoxysilane.

N15. The nanoparticle according to any of the preceding embodiments, wherein the second coating is functionalized with at least one functional group.

N16. The nanoparticle according to the preceding embodiment, wherein the functional group derived from at least one compound selected from a group consisting of an epoxide, an organo-siloxane, an epoxy-siloxane, an amino alkyl alkoxysilane, and a tetra alkyl di-siloxane.

N17. The nanoparticle according to embodiment N15, wherein the functional group derived from at least one compound selected from a group consisting of a (poly)peptide, wherein the (poly)peptide comprises at least one peptide with a molecular weight between 1 and 100 kDa, preferably between 10 and 50 kDa, such as between 20 and 40 kDa, and a (poly)saccharide, wherein the (poly)saccharide comprises at least one saccharide with a molecular weight between 100 and 2000 kDa, preferably between 200 and 1500 KDa, such as between 300 and 1200 kDa, such as between 400 and 1000 kDa.

N18. The nanoparticle according to the preceding embodiment, wherein the (poly)saccharide is at least one of dextran,
chitosan,
glycogen,
cellulose, and
alginate.

N19. The nanoparticle according to embodiment N15, wherein the functional group further comprises at least one of DNA, and
RNA.

N20. The nanoparticle according to embodiment N15, wherein the functional group further comprises at least one analgesic compound.

N21. The nanoparticle according to embodiment N15, wherein the functional group further comprises at least one of antibody, wherein the at least one antibody is for identifying lesions in tissues via antibody-binding.

N22. The nanoparticle according to the preceding embodiment, wherein the lesions are brain lesions.

N23. The nanoparticle according to any of the preceding embodiments and with features of embodiment N13, wherein the chemical bond is a covalent bond.

N24. The nanoparticle according to any of the preceding embodiments and with features of embodiment N13, wherein the chemical bond is a non-covalent bond.

N25. The nanoparticle according to any of the preceding embodiments, wherein the first coating layer comprises an inner surface and an outer surface.

N26. The nanoparticle according to the preceding embodiment and with features of N13, wherein the inner surface of the first coating layer is chemically bond to metal-based core.

N27. The nanoparticle according to any of the preceding embodiments, wherein the nanoparticle comprises a cubic crystal structure.

N28. The nanoparticle according to any of the embodiment N1 to N26, wherein the nanoparticle comprises at least one crystal structure of tetragonal,
orthorhombic,
hexagonal
trigonal,
monoclinic,
triclinic, and
primitive.

N29. The nanoparticle according to any of the 2 preceding embodiments, wherein the crystal structure comprises an edge length between 1 and 100 nm.

N30. The nanoparticle according to the preceding embodiment, wherein the edge length of the crystal structure is between 5 and 80 nm, preferably between 8 and 70 nm, such as between 10 and 60, such as between 15 and 50m, such as 20 and 40 nm.

N31. The nanoparticle according to the preceding embodiment, wherein the crystal structure of the nanoparticle comprises at least one lattice type of a body-centered,
a face-centered, and
side centered.

N32. The nanoparticle according to any of the embodiment N1 to N26, wherein the nanoparticle comprises a spherical structure with a diameter between 5 and 80 nm, preferably between 8 and 70 nm, such as between 10 and 60, such as between 15 and 50m, such as 20 and 40 nm.

N33. The nanoparticle according to any of the 5 preceding embodiments and with features of embodiment N2 or N3, wherein the nanoparticle exhibits a saturation magnetization ($M_s$) in the range of 40 to 218 emu per g-M.

N34. The nanoparticle according to any of the 6 preceding embodiments, wherein the nanoparticle exhibits a coercivity ($H_c$) lower than 0.050 T, preferably lower than 0.010 T, such as 0.019 T.

N35. The nanoparticle according to the preceding embodiment, wherein the nanoparticle is a ferromagnetic nanoparticle.

N36. The nanoparticle according to embodiment N31, wherein the nanoparticle is a ferrimagnetic nanoparticle.

N37. The nanoparticle according to any of the preceding embodiments, wherein the nanoparticle is water soluble.

N38. The nanoparticle according to any of the preceding embodiments, wherein the first coating layer covers at least 80% of a surface of the metal-based core, preferably at least 90%, more preferably at least 99%.

N39. The nanoparticle according to the preceding embodiments, wherein the nanoparticle covered with the first coating layer exhibits a saturation magnetization ($M_s$) higher than 45 emu/g-M, preferably higher than 70 emu/g-M, more preferably higher than 100 emu/g-M, such as higher than 150 emu/g-M, such as higher than 180 emu/g-M, such higher than 200 emu/g-M, such as higher than 220 emu/g-M.

N40. The nanoparticle according to any of the preceding embodiments and with features of embodiments N6 and N7, wherein the second coating layer covers at least 25% of the outer surface of the first coating layer, preferably at least 40%, more preferably at least 50%.

N41. The nanoparticle according to any of the preceding embodiments, wherein the second coating layer covers 90% or less, preferably 80% or less, more preferably 70% or less of the outer surface of the first coating.

N42. The nanoparticle according to any of the preceding embodiments, wherein the nanoparticle is water soluble and exhibits a polydispersity index (PDI) lower than 0.7, preferably lower than 0.6, more preferably lower than 0.5, such as lower than 0.4, such as lower than 0.3, such as lower than 0.2, such as lower than 0.1.

N43. The nanoparticle according to any of the preceding embodiments, wherein the nanoparticle is suitable for magnetic resonance imaging.

N44. The nanoparticle according to any of the preceding embodiments, wherein the nanoparticle is for use as a soft or field excited magnets.

N45. The nanoparticle according to the preceding embodiment, wherein the soft field is between 1 T and 20 T, preferably between 1.2 T and 15 T, more preferably between 1.5 T and 10 T.

N46. The nanoparticle according to any of the preceding embodiments and with features of embodiments N19 and N20, wherein the nanoparticle is for use in drug delivery.

N47. The nanoparticle according to any of the preceding embodiments and with features of embodiments N19 and N20, wherein the nanoparticle is for use as medicament.

Below, synthesis method embodiments will be discussed. These embodiments are abbreviated by the letter "M" followed by a number. When reference is herein made to a synthesis method embodiment, those embodiments are meant.

M1. A method for synthesizing a nanoparticle, the method comprising the steps of (i) preparing a metal oxide nanoparticle comprising a metal oxide with a chemical structure represented as $M_nO_mbH_2O$, wherein M is a transition metal, n is an integer between 1 and 5, m is an integer between 1 and 10, and b is an integer between 0 and 20, (ii) coating the metal oxide nanoparticle with a first coating layer substantially covering the metal oxide nanoparticle with a layer comprising a first compound to generate a coated metal oxide nanoparticle, (iii) reducing the coated metal oxide nanoparticle with a suitable reducing agent, wherein the reducing agent causes the metal oxide of the coated metal oxide nanoparticle to reduce substantially to a state of zero oxidation to generate a coated metal-based core nanoparticle, and (iv) coating the coated metal-based core nanoparticle with a second coating layer at least partially covering the coated metal-based core nanoparticle with a compound comprising at least one moiety to obtain a double-coated metal-based core nanoparticle.

M2. The method according to the preceding embodiment, wherein the method comprises washing a plurality of times a product obtained in at least one of the steps (i), (ii), (iii) and (iv) with a suitable washing solution.

M3. The method according to any of the two preceding embodiments, wherein in step (i) the method comprises preparing the metal oxide nanoparticle via using as a precursor a transition metal salt.

M4. The method according to the preceding embodiment, wherein the transition metal salt comprises a n-hydrate nitrate salt, such as a nonahydrate nitrate salt.

M5. The method according to any of the preceding embodiments, wherein in step (i) the transition metal is one selected from a group consisting of Fe, Co, and Ni.

M6. The method according to any of the preceding embodiments, wherein in step (i) the transition metal is one selected from a group consisting of Cu, Au, Ag, Pd, Pt, Mn, Gd, Tb, Dy, Ho, Er, Tm and Cf.

M7. The method according to any of the preceding method embodiments, wherein in step (i) the metal oxide nanoparticle comprises a cubic crystal structure.

M8. The method according to any of the embodiments M1 to M3, wherein in step (i) the metal oxide nanoparticle comprises at least one crystal structure of tetragonal,
orthorhombic,
hexagonal
trigonal,
monoclinic,
triclinic, and
primitive.

M9. The method according to any of the 2 preceding embodiments, wherein the crystal structure comprises a size with an edge length between 1 and 100 nm.

M10. The method according to the preceding embodiment, wherein the edge length of the crystal structure is between 5 and 80 nm, preferably between 8 and 70 nm, such as between 10 and 60, such as between 15 and 50m, such as 20 and 40 nm.

M11. The method according to any of the embodiments M1 to M6, wherein in step (i) the metal oxide nanoparticle comprises a spherical crystal structure with a diameter between 5 and 80 nm, preferably between 8 and 70 nm, such as between 10 and 60, such as between 15 and 50m, such as 20 and 40 nm.

M12. The method according to any of the preceding method embodiments, wherein in step (i) the method comprises preparing the metal oxide nanoparticle via one-pot pyrolysis.

M13. The method according to any of the embodiments M1 to M11, wherein in step (i) the method comprises preparing the metal oxide nanoparticle via solvothermal synthesis.

M14. The method according to any of the 2 preceding embodiments, wherein preparing the metal oxide comprises a synthesis temperature in the range of 50 to 800° C., preferably between 80 and 500° C., more preferably between 100 and 200° C.

M15. The method according to any of the 3 preceding embodiments, wherein preparing the metal oxide comprises a synthesis pressure lower than 10 MPa, preferably lower than 5 MPa, more preferably lower than 1 MPa, such as lower than 0.8 MPa, such as lower than 0.6 MPa, such as 0.1 MPa.

M16. The method according to any of the preceding method embodiments, wherein in step (i) the method comprises controlling the size of the metal oxide nanoparticles via addition of at least one size-controlling agent comprising at least one compound with a molecular weight between 1 and 100 kDa, preferably between 5 and 80 kDa, more preferably between 10 and 40 kDa.

M17. The method according to the preceding embodiment, wherein the size-controlling agent comprises at least one of polyvinylpyrrolidone (PVP),
polyethylene glycol (PEG),
acetyl acetate, and
a surfactant oleic acid.

M18. The method according to any of the preceding method embodiments, wherein step (i) is performed in a reaction medium comprising at least one compound comprising at least one of N, N-dimethylformamide (DMF),
dimethyl sulfoxide (DMSO),
ethanol, and
water.

M19. The method according to any of the preceding method embodiments, wherein in step (ii) the silane-based compound comprises a compound represented in formula 3

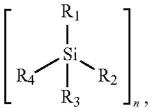

wherein n is an integer greater than or equal to 0 and less than or equal to 20, and $R_1$, $R_2$, $R_3$, and $R_4$ comprise each and independently at least one moiety selected from a group consisting of —CHO, —CON, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nN_{2n}$ wherein n is an integer greater than or equal to 0 and less than or equal to 20, and —COX wherein X is one of F, Cl, Br, and I.

M20. The method according to any of the preceding method embodiments, wherein in step (iii) the suitable reducing agent comprising at least one of $CaH_2$, NaH, LiH, $LiAlH_4$, $Mn^{2+}$, Mg or $H_2$ gas, a metal from AI and/or AII group, and a halogen from VII group.

M21. The method according to any of the preceding method embodiments, wherein in step (iv) the at least one moiety comprises a moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than or equal to 0 and less than or equal to 15, and —COX wherein X is one of F, Cl, Br, and I.

M22. The method according to any of the embodiments M1 to M20, wherein in step (iv) the at least one moiety comprises at least one compound represented in Formula 2

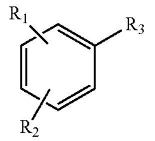

wherein $R_1$, and $R_2$ comprise each and independently at least one moiety selected from a group consisting of —OH, —COOH, —$NH_2$, —SH, —$CONH_2$, —OX, and —COX, wherein X is a halogen selected from a group consisting of F, Cl, Br, and I, and wherein $R_3$ comprises independently from $R_1$ and $R_2$ at least one moiety selected from a group consisting of —CHO, —COH, —COOH, —SH, —$CONH_2$, —$PO_3H$, —$OPO_4H$, —$SO_3H$, —$OSO_3H$, —$N_3$, —OH, —SS—, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than or equal to 0 and less than or equal to 15, and —COX wherein X is one of F, Cl, Br, and I.

M23. The method according to the preceding embodiment and with features of embodiments M19, wherein the method comprises linking the compound represented in formula 2 to the first coating layer comprising the compound represented in Formula 3 via at least one of $R_1$ and $R_2$ of the compound represented in Formula 2.

M24. The method according to the preceding embodiment, wherein the second-coated metal-based core nanoparticle comprises a cubic crystal structure with an edge length between 1 and 100 nm.

M25. The method according to any of the preceding embodiment, wherein the edge length of the cubic crystal structure is between 5 and 80 nm, preferably between 10 and 60 nm, such as 15 nm.

M26. The method according to any of the preceding method embodiments and with features of embodiment M16, wherein one or more of the at least one size-controlling compound is a dispersant.

M27. The method according to any of the preceding method embodiments, wherein in step (i) the method comprises controlling the size of the metal oxide nanoparticle via controlling the controlling a stoichiometric ratio of at least one of the metal oxide, and the size-controlling agent.

M28. The method according to the preceding embodiment, wherein the stoichiometric ratio between the size-controlling agent and the metal oxide is A:B, wherein A is the size-controlling agent and B is the metal oxide, wherein the stoichiometric ratio is in the range of 1:3 to 1:150, preferably between 1:4 to 1:120, more preferably between 1:4 to 1:110, such 1:5 to 1:120, such as 1:5 to 1:110, such as 1:6 to 1:100, such as 1:8 to 1:90, such as 1:10 to 1:50, such as 1:12 to 1:40.

M29. The method according to any of the 2 preceding embodiments, wherein the step of controlling the size of the metal oxide nanoparticle comprises controlling the synthesis temperature, wherein the synthesis temperature is between 120 and 220° C., preferably between 140 and 200° C., more preferably between 150 and 190° C., such as 160° C.

M30. The method according to any of the preceding method embodiments, wherein in step (ii) the method comprises reducing the metal oxide nanoparticle, whereby the edge length or the diameter of the nanoparticle increases in a range lower than 20% of the initial edge length or the diameter, preferably lower than 10%, more preferably lower than 5% of the initial edge length or the diameter.

M31. The method according to any of the preceding method embodiments, wherein in step (iii) the method comprises reducing the coated metal oxide with a reduction temperature lower than 1000° C., preferably lower than 800° C., more preferably lower than 500° C.

M32. The method according to any of the preceding method embodiments, wherein in step (iii) the method comprises reducing the coated metal oxide with a reduction pressure lower than $10^{-3}$ Pa, preferably lower than $10^{-4}$ Pa, more preferably lower than $10^{-5}$ Pa, such as lower than $10^{-6}$ Pa.

M33. The method according to any of the preceding method embodiments, wherein the method is suitable for preparing the nanoparticle for use in magnetic resonance imaging.

M34. The method according to any of the preceding method embodiments, wherein the method is suitable for preparing the nanoparticle for use in magnetic separation.

M35. The method according to any of the preceding method embodiments, wherein the method is suitable for preparing the nanoparticle for use in drug delivery.

Below, contrast agent embodiments will be discussed. These embodiments are abbreviated by the letter "A" followed by a number. When reference is herein made to a contrast agent embodiment, those embodiments are meant.

A1. A contrast agent comprising a nanoparticle according to any of the preceding nanoparticle embodiments.

A2. The contrast agent according to the preceding embodiment, wherein the contrast agent further comprises a suitable medium for dispersing the nanoparticles, wherein the suitable medium causes the nanoparticle to disperse, thereby forming a contrast agent solution.

A3. The contrast agent according to the preceding embodiment, wherein the contrast agent is for use in magnetic resonance imaging.

A4. The contrast agent according to the preceding embodiment, wherein the use of the contrast agent in magnetic resonance imaging is for medical treatment.

A5. The contrast agent according to any of the preceding contrast agent embodiments, wherein the contrast agent is for use in whole-body imagining.

A6. The contrast agent according to any of the preceding contrast agent embodiments, wherein the contrast agent is for use in organ imaging.

A7. The contrast agent according to any of the preceding contrast agent embodiments, wherein the contrast agent is for use in characterization of soft tissues.

A8. The contrast agent according to any of the preceding contrast agent embodiments, wherein the contrast agent is for use in diagnosis of tumors and/or metastasis in liver and/or spleen.

A9. The contrast agent according to any of the preceding contrast agent embodiments, wherein the contrast agent is for use in brain imaging.

A10. The contrast agent according to the preceding embodiment, wherein the contrast agent is for use in brain imaging for tumors.

A11. The contrast agent according to embodiment A9, wherein the contrast agent is for use in brain imaging for Alzheimer's disease.

A12. The contrast agent according to any of the preceding contrast agent embodiments, wherein the contrast agent is for use in preliminary diagnosis of Parkinson's disease.

A13. The contrast agent according to any of the preceding contrast agent embodiments, wherein the contrast agent is for use in preliminary diagnosis of Multiple Sclerosis (MS).

Below, composition embodiments will be discussed. These embodiments are abbreviated by the letter "C" followed by a number. When reference is herein made to a composition embodiment, those embodiments are meant.

C1. A composition comprising a nanoparticle according to any of the preceding nanoparticle embodiments.

C2. The composition according to the preceding embodiment, wherein the composition is configured to target a targeting group comprising at least one of liver, spleen, kidney, blood, heart and brain cells.

C3. The composition according to any of the 2 preceding embodiments, wherein the composition is configured for use as a contrast agent according to any of the preceding contrast agent embodiments for magnetic resonance imaging.

Below, pharmaceutical composition embodiments will be discussed. These embodiments are abbreviated by the letter "P" followed by a number. When reference is herein made to a pharmaceutical composition embodiment, those embodiments are meant.

P1. A pharmaceutical composition comprising a nanoparticle according to any of the preceding nanoparticle embodiments.

P2. The pharmaceutical composition according to the preceding embodiment, wherein the pharmaceutical composition comprises at least one dispersing agent.

P3. The pharmaceutical composition according to any of the 2 preceding embodiments, wherein the pharmaceutical composition comprises at least one excipient.

P4. The pharmaceutical composition according to any of the preceding pharmaceutical composition embodiments, wherein the pharmaceutical composition is for use as a medicament.

P5. The pharmaceutical composition according to any of the preceding pharmaceutical composition embodiments, wherein the pharmaceutical composition is for treatment of liver disease.

P6. The pharmaceutical composition according to any of the preceding pharmaceutical composition embodiments, wherein the pharmaceutical composition is for treatment of cancer and/or metastatic cancer.

P7. The pharmaceutical composition according to any of the preceding pharmaceutical composition embodiments, wherein the pharmaceutical composition is for treatment of hypothermia.

P8. The pharmaceutical composition according to any of the preceding pharmaceutical composition embodiments, wherein the pharmaceutical composition is for photodynamic therapy.

Below, image obtaining method embodiments will be discussed. These embodiments are abbreviated by the letter "I" followed by a number. When reference is herein made to an image obtaining method embodiment, those embodiments are meant.

I1. A method for obtaining a magnetic resonance image, the method comprising

- administering a contrast agent according to any of the preceding contrast agent embodiments to a subject selected to undergo magnetic resonance imaging, and
- acquiring a contrast-enhanced magnetic resonance image of the subject.

I2. The method according to the preceding embodiment, wherein the step of administering the contrast agent comprises administering the contrast agent via injection.

I3. The method according to embodiment I, wherein the step of administering the contrast agent comprises administering the contrast agent via an oral administration.

I4. The method according to any of the preceding imaging obtaining method, wherein the step of acquiring a contrast-enhanced magnetic resonance image comprises at least one of

- a T1-weighted scan, and
- a T2-weighted scan.

Below, contrast-enhanced method embodiments will be discussed. These embodiments are abbreviated by the letter "E" followed by a number. When reference is herein made to a contrast-enhanced method embodiment, those embodiments are meant.

E1. A method of contrast-enhanced magnetic resonance imaging, wherein the method comprises

- using the contrast agent according to any of the preceding contrast agent embodiments for generating a magnetic resonance image with an increased relaxivity of a targeting group during a relaxation portion of a magnetic resonance image pulse, wherein the increased relaxivity is achieved via the nanoparticle comprised in the contrast agent.

E2. The method according to preceding embodiment, wherein the method comprises executing an image obtaining method according to any of the preceding image obtaining method embodiments.

E3. The method according to any of the 2 preceding embodiments, wherein the comprises carrying at least one of

- a T1-weighted scan, and
- a T2-weighted scan.

E4. The method according to the preceding embodiment, wherein the at least one scan is carried out at a plurality of different times, wherein the different times comprise at least one of

- an initial time $t_0$,
- at least one subsequent time $t_n$.

E5. The method according to the preceding embodiment, wherein the at least one scan at the initial time $t_0$ is performed before injecting the contrast agent to a subject selected to undergo magnetic resonance imaging.

E6. The method to any of the 2 preceding embodiments, wherein the at least one scan at the subsequent time $t_n$ is performed after injecting the contrast agent to the subject selected to undergo magnetic resonance imaging.

E7. The method according to the preceding embodiment, wherein the at least one scan at the subsequent time $t_n$ at least one time of a time $t_1$ carried out after 10 min of the injection of the contrast agent, a time $t_2$ carried out after 50 min of the injection of the contrast agent, a time $t_3$ carried out after 3 h of the injection of the contrast agent, a time $t_4$ carried out after 21 h of the injection of the contrast agent, and a time $t_5$ carried out after 1 week of the injection of the contrast agent.

E8. The method according to any of the preceding contrast-enhanced method embodiments, wherein the at least one scan at the initial time $t_0$ and subsequent time $t_n$ is for use in medical diagnosis.

Below, treatment method embodiments will be discussed. These embodiments are abbreviated by the letter "T" followed by a number. When reference is herein made to a treatment method embodiment, those embodiments are meant.

T1. A method for treating a medical disease, the method comprising the nanoparticle according to any of the preceding nanoparticle embodiments or the pharmaceutical composition according to any of the preceding pharmaceutical composition embodiments, wherein the method comprises administrating the nanoparticle or pharmaceutical composition to a subject.

T2. The method according to the preceding embodiment, wherein the method comprises a route of administration, wherein the route of administration comprises at least one of oral, and intravenous.

T3. The method according to any of the two preceding embodiments, wherein the method comprises a target action comprising at least one of topical, enteral, and parenteral.

T4. The method according to the preceding embodiment, wherein the parenteral target action comprises at least one of intradermal, subcutaneous, intramuscular, intraperitoneal, and intravenous.

T5. The method according to any of the preceding treatment embodiments, wherein the method is for treatment of hypothermia.

T6. The method according to any of the preceding treatment embodiments, wherein the method is for treatment of liver's diseases.

T7. The method according to any of the preceding treatment embodiments, wherein the method is for treatment of lung's diseases.

T8. The method according to any of the preceding treatment embodiments, wherein the method is for treatment of cancer.

T9. The method according to any of the preceding treatment embodiments, wherein the method is for treatment of Alzheimer's disease.

T10. The method according to any of the preceding treatment embodiments, wherein the method is for treatment of Multiple Sclerosis.

T11. The method according to any of the preceding treatment embodiments, wherein the method is for treatment of Parkinson's diseases.

Below, use embodiments will be discussed. These embodiments are abbreviated by the letter "U" followed by a number. When reference is herein made to a use embodiment, those embodiments are meant.

U1. Use of the contrast agent according to any of the preceding contrast agent embodiment.

U2. The use according to the preceding embodiment, wherein the contrast agent is used for diagnosing Alzheimer's disease.

U3. The use according to any of the two preceding embodiments, wherein the contrast agent is used for diagnosing Parkinson's disease.

U4. The use according to any of the preceding use embodiments, wherein the contrast agent is used for diagnosing strokes.

U5. The use according to any of the preceding use embodiments, wherein the contrast agent is used for diagnosing liver disease.

U6. The use according to any of the preceding use embodiments, wherein the contrast agent is used for diagnosing Multiple Sclerosis (MS).

The present invention will now be described with reference to the accompanying drawings which illustrate embodiments of the invention. These embodiments should only exemplify, but not limit, the present invention.

Figure 4:
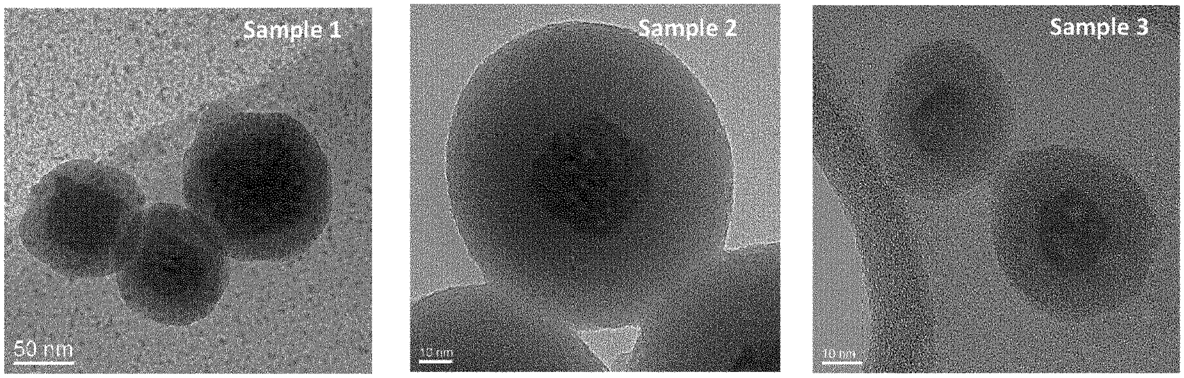
Figure 5:
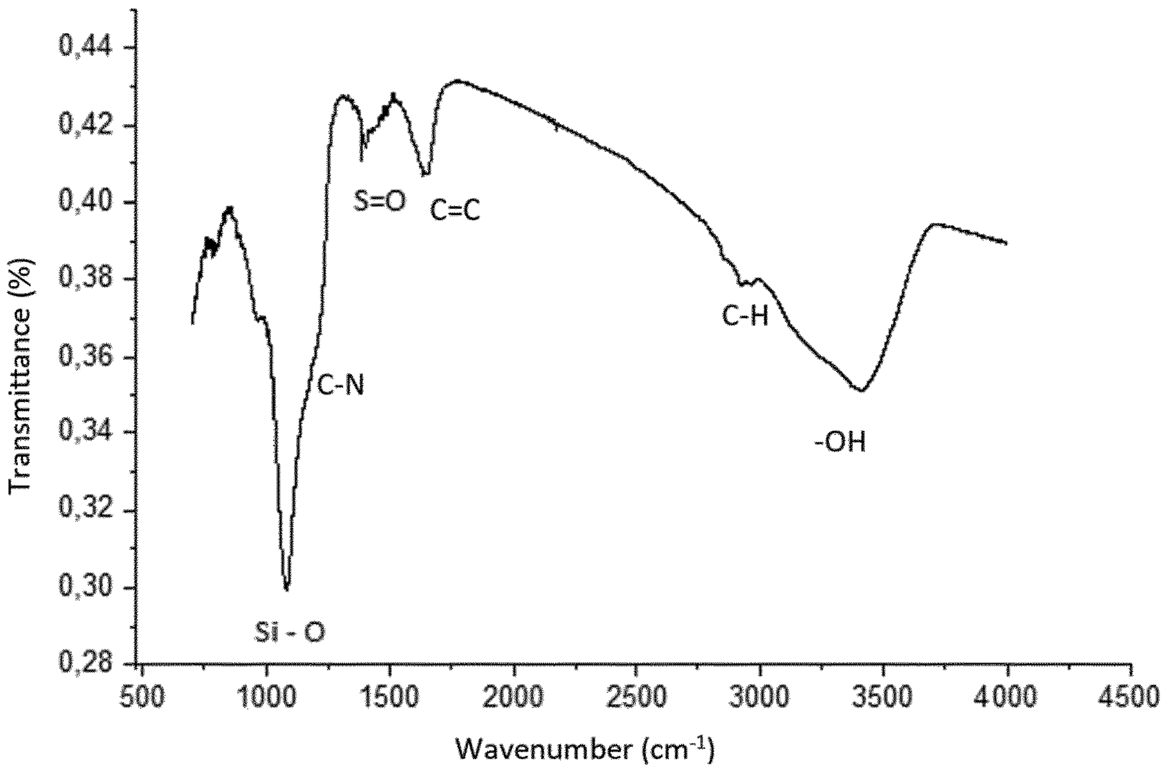
Figure 6:
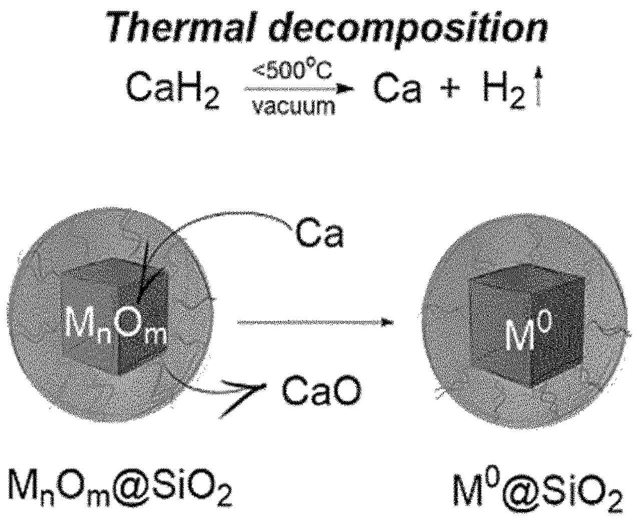
Figure 7:
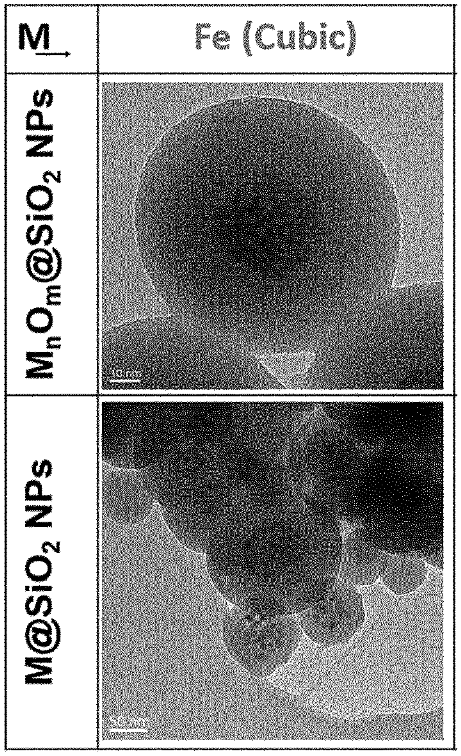
Figure 8:
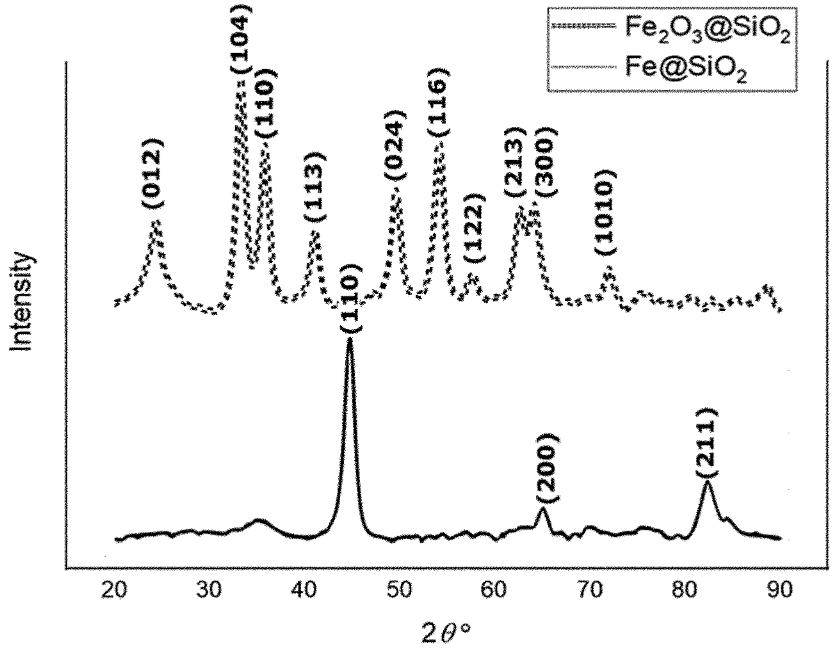
Figure 9:
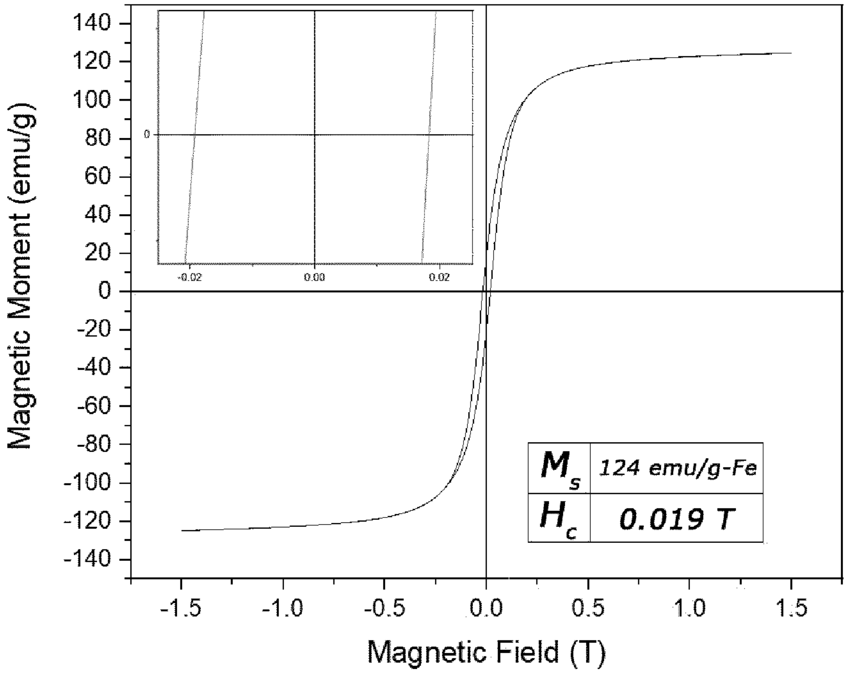
Figure 10:
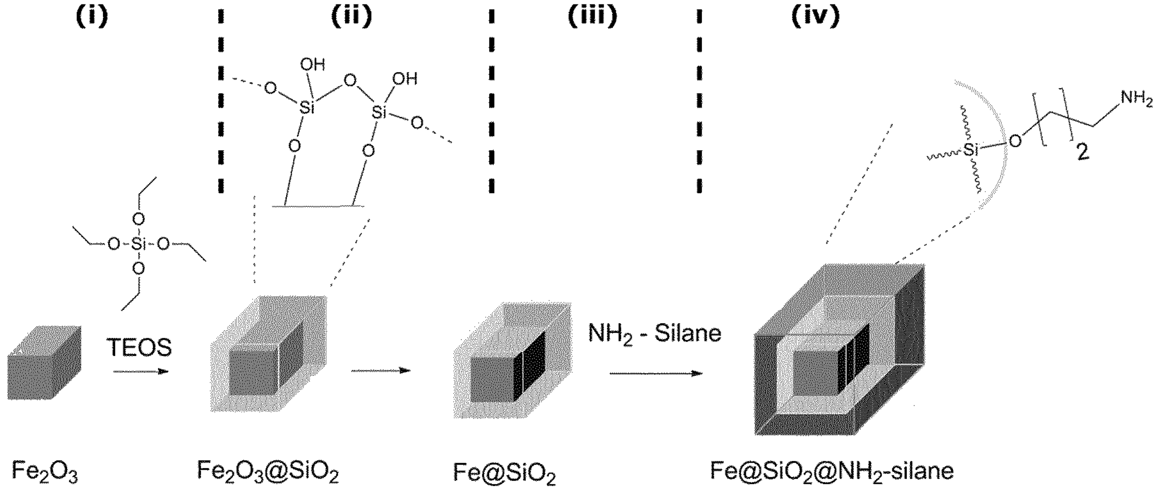
Figure 11:
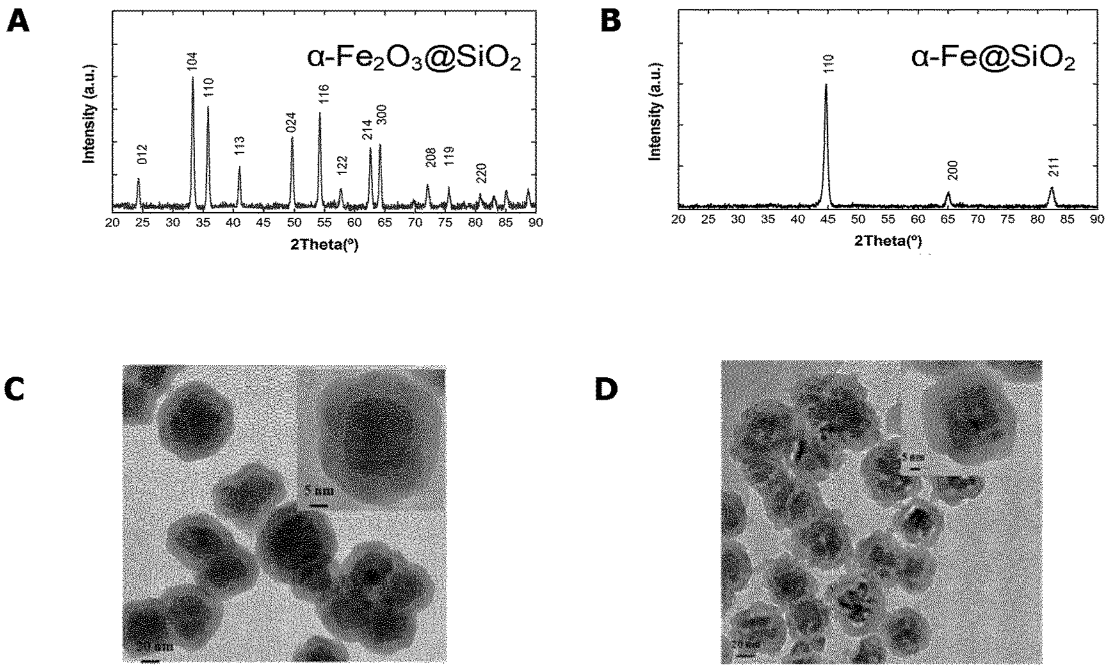
Figure 12:
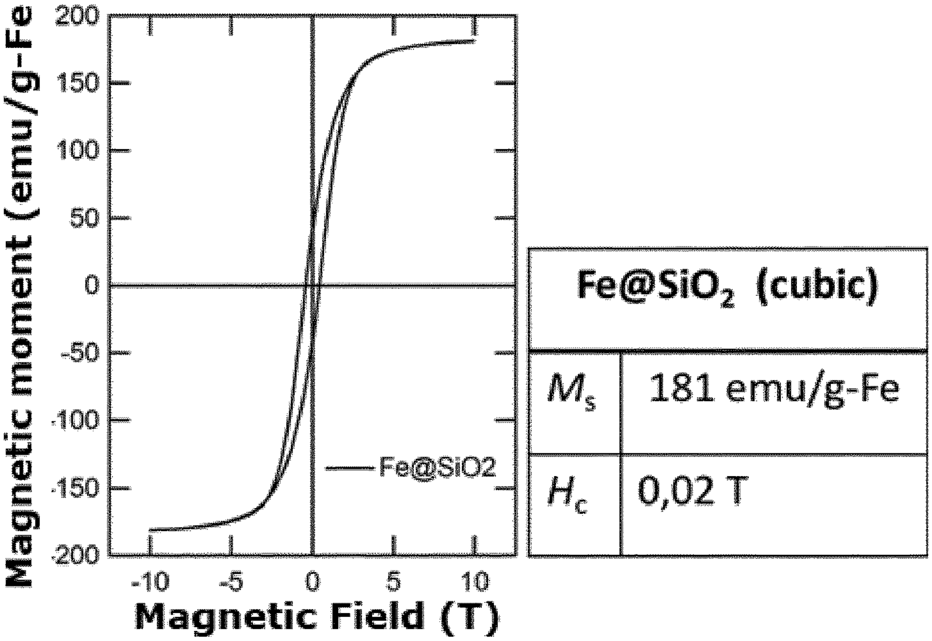
Figure 13:
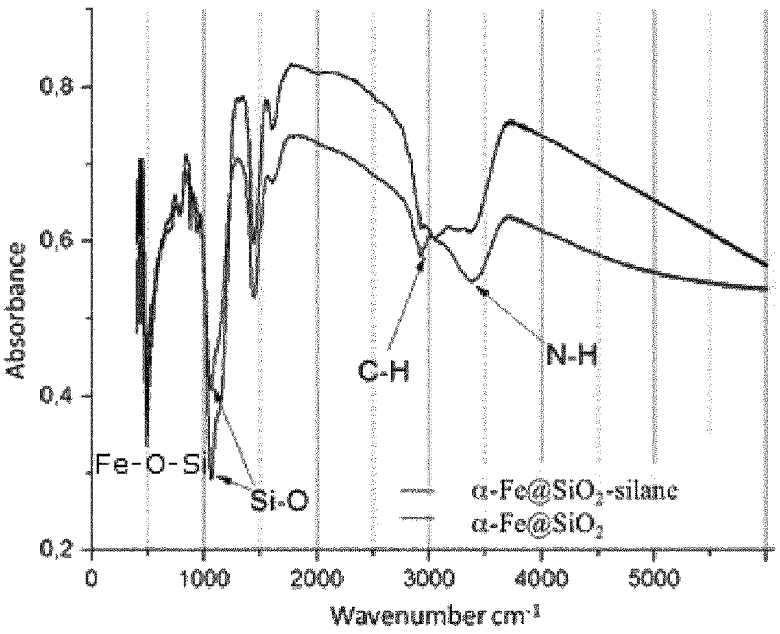
Figure 15:
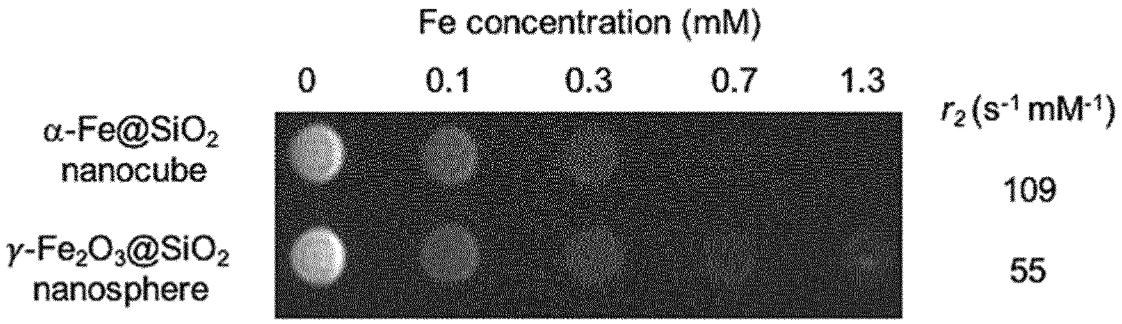
Figure 16:
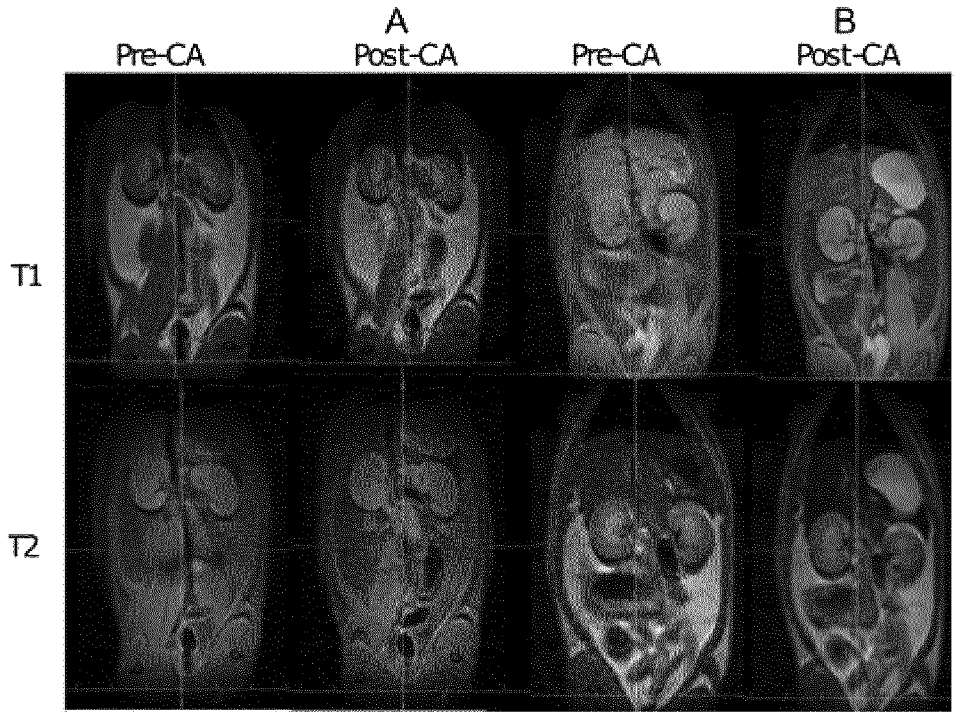
Figure 17:
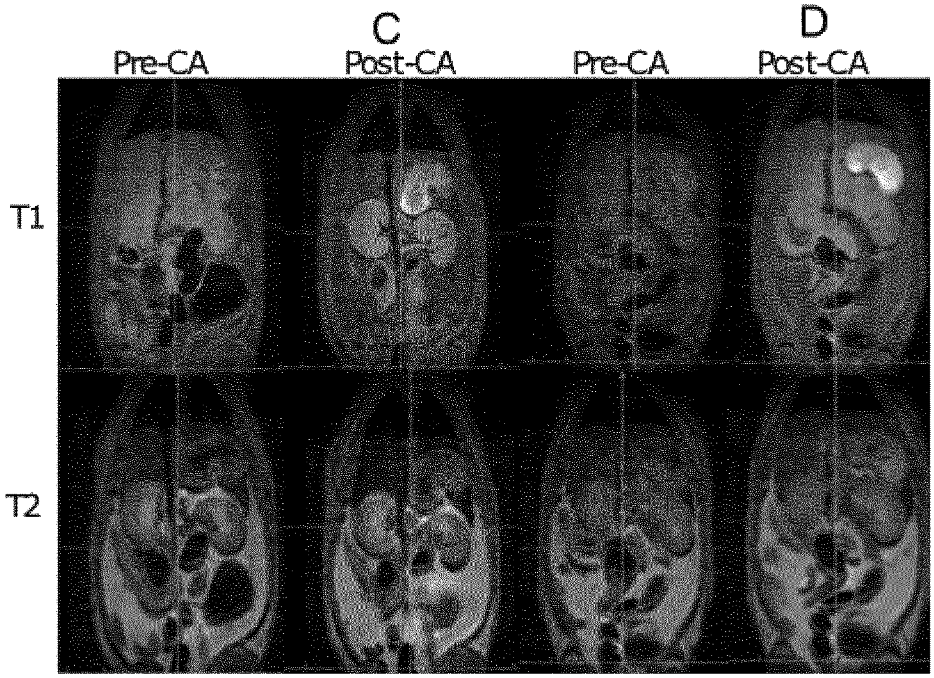
Figure 18:
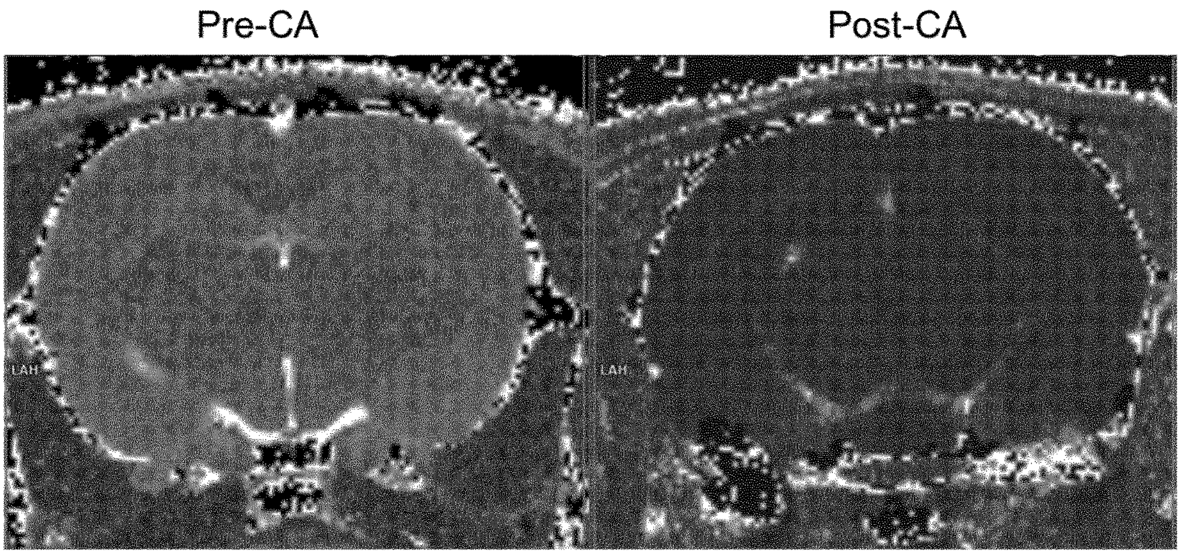
Figure 19:
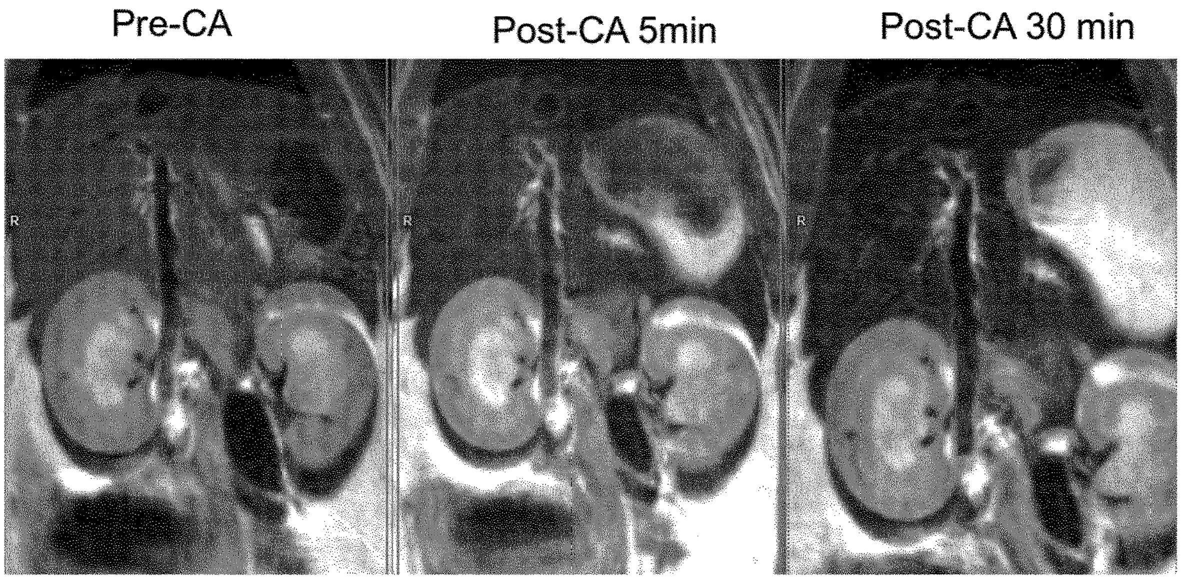

FIG. 4 depicts TEM images of sample 1, sample 2 and sample 3 of a nanoparticle according to embodiments of the present invention;

FIG. 5 depicts an IR spectrum of a nanoparticle coated with a first layer of silicon dioxide and a second layer of zwitterionic dopamine sulfonate according to embodiments of the present invention;

FIG. 6 depicts thermal decomposition and a reduction mechanism according to embodiments of the present invention;

FIG. 7 depicts TEM images a metal oxide nanoparticle coated with silicon dioxide and a metal nanoparticle coated with silicon dioxide according to embodiments of the present invention;

FIG. 8 depicts PXRD patterns of nanoparticles coated with silicon dioxide before and after a step (iii) according to embodiments of the present invention;

FIG. 9 depicts saturation magnetization (Ms) and coercivity field ($H_c$) of coated metal-based core according to embodiments of the present invention;

FIG. 10 depicts a synthesis steps of a nanoparticle coated with a first siloxane layer and a second layer of an amino silane according to embodiments of the present invention;

FIG. 11A-B depict PXRD patterns for nanoparticles according to embodiments of the present invention;

FIG. 11 C-D depict TEM images for nanoparticles according to embodiments of the present invention;

FIG. 12 depicts a magnetic hysteresis curve of a magnetic measurement of $\alpha$-Fe@$SiO_2$ according to embodiments of the present invention;

FIG. 13 depicts FTIR spectra of metal-based nanoparticles coated with an amino silane layer according to embodiments of the present invention;

FIG. 14*a* depicts PXRD patterns for a spherical maghemite coated with $SiO_2$ ($\gamma$-$Fe_2O_3$@$SiO_2$);

FIG. 14*b* depicts TEM images for a spherical maghemite coated with $SiO_2$ ($\gamma$-$Fe_2O_3$@$SiO_2$);

FIG. 15 depicts a $r_2$ relaxivity value for $\alpha$-Fe@$SiO_2$ and $\gamma$-$Fe_2O_3$@$SiO_2$ nanoparticles according to embodiments of the present invention;

FIG. 16A-B depict T1 and T2-weighted magnetic resonance imaging scans of rat's body pre and post contrast agent injection according to embodiments of the present invention;

FIG. 17C-D depict T1 and T2-weighted magnetic resonance imaging scans of rat's body pre and post contrast agent injection according to embodiments of the present invention;

FIG. 18 depict T1 and T2-weighted magnetic resonance imaging scans of a rat's brain pre and post contrast agent injection according to embodiments of the present invention;

FIG. 19 depicts time dependence in vivo magnetic resonance imaging pre and after injection of a subject with silicon dioxide coated iron nanoparticles according to embodiments of the present invention;

It is noted that not all the drawings carry all the reference signs. Instead, in some of the drawings, some of the reference signs have been omitted for sake of brevity and simplicity of illustration. Embodiments of the present invention will now be described with reference to the accompanying drawings.

Figure 1:
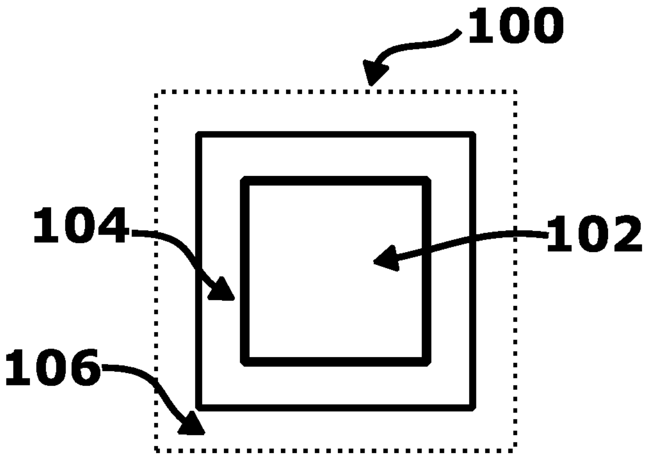
FIG. 1 depicts a frontal view of a nanoparticle according to embodiments of the present invention.

FIG. 1 depicts a frontal view of a nanoparticle 100 according to embodiments of the present invention. In simple terms, the nanoparticle 100 may comprise a core, a first layer surrounding the core and a second layer surrounding the first layer, conceptually identified by reference numerals 102, 104 and 106, respectively.

In one embodiment, the nanoparticle 100 may comprise a core 104 comprising a metal-based core, for instance, a transition metal. While all examples here are given based on an iron-based core, it should be understood that other metals may be possible, for instance, the core 102 may comprise other metals or at least other transition metals, e.g. a metal from a transition series such as a metal from the first transition series, for instance, but not limited, cobalt and nickel. Therefore, the core 102 may also be referred to as metal-based core 102 or metallic core 102. Furthermore, the metal-based core 102 may comprise at least one nanostructure such as a nano sphere, a nano cube.

Moreover, the nanoparticle 100 may comprise a first coating layer 104 covering substantially the metal-based core 102. The first coating layer may also be referred to as first layer 104 or first coating layer 104. In other words, the first coating layer 104 may comprise a functional layer configured to protect the metal-based core 102 from the surrounding environment. For instance, in one embodiment of the present invention, the metal-based core 102 may comprise a metal with an oxidation state of zero, which in some instances may be particular advantageous, as it may possess physical, chemical and/or physicochemical properties that may allow to utilize the nanoparticle 100 in a plurality of applications, such as in technological fields where magnetic properties of materials play a crucial role, e.g. in magnetic resonance.

In one embodiment, the first coating layer 104 may comprise, for example, a silane-based coating. In simple terms, a silane-containing compound such an alkoxide of silicon, e.g. tetraethyl orthosilicate (TEOS), may be added to a reaction medium, e.g. a solvent, for instance, dropwise. The metal-based core 104 may, for example, be submerged in the reaction medium, wherein the metal-based core 104 may undergo a sol-gel reaction, whereby the silane-containing compound may react with the surface of the metal-based core 104 to form a first coating layer 104.

It should be understood that due to a typically high reactivity of metal-based core, the metal-based core 104 may, in fact, comprise a metal oxide-based core that may be coated with the silane-containing compound, wherein the coated metal oxide-based core may subsequently be subjected to a reduction process, whereby the metal oxide-based core may be reduced to an oxidation state of zero to obtain the coated metal-based core 104'.

It should also be understood that the first coating layer 104 may comprise a monolayer and/or a multilayer coating. For instance, in the case that the first coating layer 104 is formed of a silane-containing compound as a precursor, the silane-containing compound may build up one or more layers of coating, wherein the one or more coating layers may comprise siloxane linkages, e.g. the first coating layer 104 may comprise a metal-coating interface, wherein a metal-siloxane bonding may be observed. Such a linkage may in some instances be particularly advantageous, as it may yield a coating layer chemically linked to the metal oxide-based core, which may allow in a subsequent step to reduce the metal oxide-based core to obtain the metal-based core 102 coated with the first coating layer 104. Therefore, the metal-based core 102 (substantially) covered with the first coating layer 104 may also be referred to as first-coated metal-based core 104' or simply as coated metal core 104', which prior to being subjected to a reduction process may be referred to as coated metal oxide-based core. Moreover, the first coating layer 104 may allow hindering any re-oxidation processes that may change the oxidation state of the metal-based core 102, i.e. it may allow to isolate the metal-based-core 102 from the surrounding, which may be beneficial to avoid oxidation of the core 102.

In one embodiment, the coated metal core 104' may be at least partially covered by a second coating layer 106. In simple terms, the second coating layer 106 may comprise a compound comprising at least one functional group that may be tunable, a feature that may allow conferring specific properties to the nanoparticle 100, wherein the at least one functional group may, for instance, increase the affinity of the nanoparticle particle to a given medium, such as water, which may subsequently allow formation of, for example, a solvation shell, which may consequently facilitate dispersing the nanoparticle 100 in said medium, i.e. in this example, in water.

In other words, the nanoparticle 100 may be a functional nanomaterial comprising a metal-based core 102 with a (defined) geometry comprising at least one dimension in the nano scale and wherein the metal-based core 102 may comprise metal with a specific property, for instance, a high saturation magnetization ($M_s$), which may allow the application of the nanoparticle 100 in a plurality of fields, such as in magnetic resonance. In an embodiment of the present invention, the geometry of the nanoparticle may comprise a cubic structure, wherein at least one edge length of the cubic structure is in the nano scale.

Furthermore, the metal-based core 102 may comprise a transition metal, such as iron, cobalt, nickel. Having a transition metal-based core 102 may be particularly beneficial, as it may allow utilizing properties of transition metals, such as, for example, using a plurality of starting metal oxides, as transition metals are well-known for forming compounds in many oxidation states as a consequence of their relatively low energy gap between feasible oxidation states. This property may be particularly advantageous, as it may allow obtaining reproducible metal-based cores 102 from a plurality of starting materials, for instance, it may be possible to obtain a metal-based core 102 from ferrous oxides as well as from ferric oxides. It should be understood that the metal-based core 102 may also be synthesized starting from different compounds of the metal transition, e.g. it may possible to obtain a ferric oxide starting from a ferric nitrate to later reduce to metallic iron.

The first coating layer 104 may substantially cover the metal-based core 102, which allow isolating the metal-based core 102 from the surrounding environment. The first coating layer 104 may, for instance, be a siloxane-based layer comprising a compound with a chemical structure as represented in formula 1

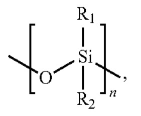

wherein n is an integer between 1 and 15, and $R_1$ and $R_2$ are each a moiety that is independently selected from a plurality of functional groups. For instance, in one embodiment, the siloxane-based layer may comprise a binding a silane-based compound such as tetraethyl orthosilicate (TEOS) on the surface of the iron oxide nanoparticle. Hence, the TEOS may form a siloxane-based layer on the iron oxide nanoparticle, as depicted in step (ii) of FIG. 2.

Example 1: Synthesis and Magnetism of Cubic $Fe^0@SiO_2$ Nanoparticles Coated with Zwitterionic Dopamine Sulfonate FIG. 2 schematically depicted a plurality of steps (i), (ii), (iii) and (iv) followed sequentially to synthesize an iron nanoparticle coated with a first layer of silicon dioxide and a second layer comprising a zwitterionic dopamine sulfonate.

Figure 2:
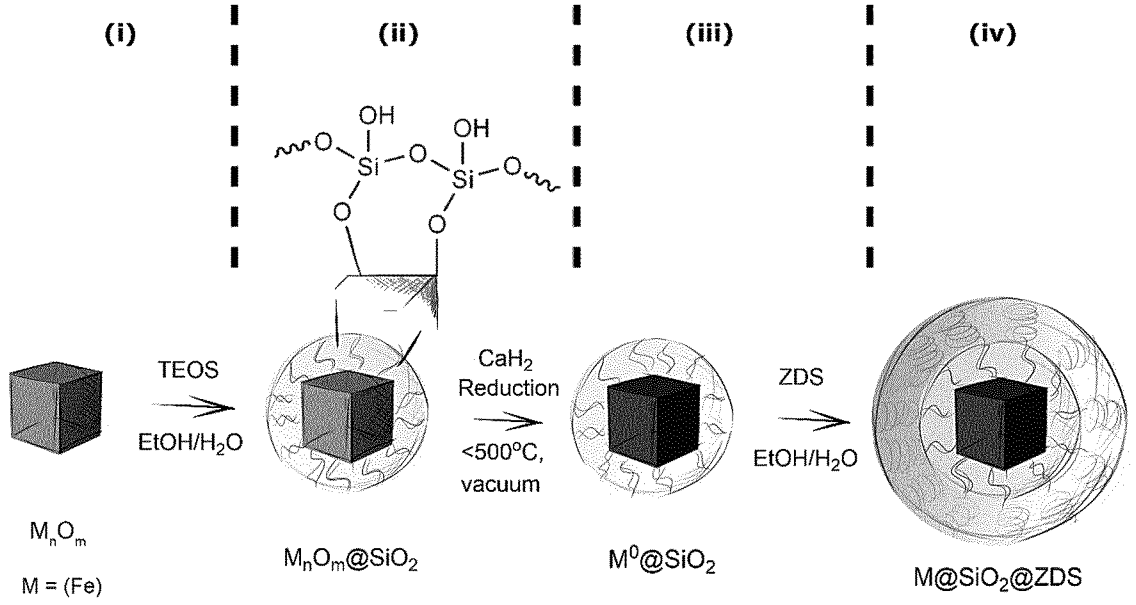
FIG. 2 depicts synthesis steps of a nanoparticle coated with a first layer of silicon dioxide and a second layer of a zwitterionic dopamine sulfonate according to embodiments of the present invention.

FIG. 2 (i) schematically depicted a first step (i), iron oxide ($Fe_2O_3$) were synthesized as cubic nanoparticles synthesis of approximated 25 nm via the method explained hereon. The Cubic Iron Oxide Nanoparticles were synthesized by thermal decomposition, wherein a solution of iron (III)nitrate n-hydrate ($Fe(NO_3)_3*nH_2O$, 99.999%, Aldrich). 3 g of $Fe(NO_3)_3*nH_2O$ was obtained by dissolving in 1.5 mL of anhydrous dimethylformamide (DMF, 99.8%, Sigma-Aldrich). Subsequently, a reaction mixture was prepared by adding 0.5 g of polyvinylpyrrolidone (PVP, Sigma-Aldrich) to the solution and stirred for 30 min. The reaction mixture was maintained at 160° C. for 2 h.

Figure 3:
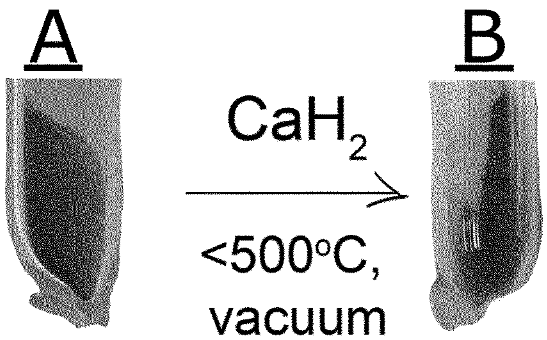
FIG. 3 depicts a color transition of a reaction mixture according to embodiments of the present invention.

Initially, as depicted in FIG. 3, the reaction mixture was red-brown (FIG. 3A) which became a light brown gradually turning into a black-brown (FIG. 3B), which may also be referred to as final solution, final black-brown solution, final black-brown colloid solution, final black-brown mixture, final black-brown colloid solution or simply final mixture. Furthermore, the final black-brown colloid solution was stirred for another 1 h, cooled to room temperature, and destabilized by adding 50 mL of ethanol, which formed a precipitate comprising nanoparticles. The precipitate was collected via centrifugation and washed twice to remove excess of surfactants and/or reaction byproducts. Collected nanoparticles were kept in ethanol solution.

FIG. 2 (ii) schematically depicted a second step (ii), the iron oxide nanoparticles were coated with silicon dioxide ($SiO_2$) via the method explained hereon. A water-ethanol solution was prepared by stirring 100 mL of ethanol and 10 mL of purified water at 200 rpm for 10 min. 25 mg of nanoparticles were dissolved in ethanol (2 ml) and added to the water-ethanol solution and stirred for 30 min. Afterwards, 2.5 mL of a ammonium hydroxide solution ($NH_4OH$ (28% w/w)) was added drop wise to the solution water-ethanol solution containing the nanoparticles, and stirred for 30 min. In parallel, a tetraethyl orthosilicate (TEOS) solution was prepared by dissolving 1 mL of TEOS in 30 mL ethanol and stirred for 30 min to obtain a TEOS-ethanol solution.

Then 4 mL of the TEOS-ethanol solution was added drop wise for 8 h to the nanoparticle solution, which yielded a precipitate comprising nanoparticles coated with $SiO_2$, which may also be referred to as coated nanoparticles. The precipitate was collected via centrifugation and washed several times, e.g. twice, to remove excess of surfactants and/or reaction byproducts. The collected coated nanoparticles were kept in ethanol solution.

FIG. 2 (iii) schematically depicted a third step (iii), the iron oxide nanoparticles coated with silicon dioxide ($Fe_2O_3@SiO_2$) were reduced with calcium hydride ($CaH_2$) via the $CaH_2$ method. It should be understood that ferric oxide nanoparticles it merely exemplary, and other oxides may also be suitable, for instance, oxides comprising other oxidation states of a metal and/or a plurality of different metal comprising a similar oxidation state, for instance, inter alia, oxides of cobalt and nickel. Preparations were made in a glove box and reaction was proceeded in a Pyrex tube. $Fe_2O_3@SiO_2$ powder was mixed with $CaH_2$ in a proportion 1:4 and crushed together to obtain a powder mixture, which was then moved to a Pyrex tube. Afterwards, the Pyrex tube, which may also be referred to as reaction tube, was sealed under vacuum as depicted in FIG. 3. The reaction tube was moved to a furnace maintaining a reaction temperature at 300° C. for several days to obtain reduced nanoparticles. The reduce nanoparticles were washed via a magnet wash, which carried out in a solution of ammonium chloride, which was prepared by dissolving ammonium chloride ($NH_4Cl$) in methanol in a proportion of 1:4. In other words, the reduced nanoparticles were washed with the $NH_4Cl$ solution by adding the reduced nanoparticles (as powder) to the solution in a baker, and placing a magnet near to the baker's wall, which allow to collected the nanoparticles, as they are magnetic. The $NH_4Cl$ solution was disposed and the nanoparticles were washed further with ethanol.

FIG. 2 (iv) schematically depicted a fourth step (iv), the iron nanoparticles coated with silicon dioxide were coated with a zwitterionic Dopamine Sulfonate (ZDS), which was synthesized via the method explained hereon.

On a first synthesis step as described by Wey at al. (Nano Lett. 12 22-25 2012) of step (iv), a dopamine sulfonate was obtained via preparing a solution of dopamine by dissolving 1.1376 g (6 mmol) of dopamine hydrochloride in 150 mL ethanol in a 500 mL round bottom flask. The flask was evacuated and back-filled with Argon, followed by slow addition of the ammonium hydroxide 28 w/w % (416 μL, 3 mmol) and 1,3-propanesultone (799 mg, 6.5 mmol). The solution was heated to 50° C. and stirred for 18 h, yielding a white precipitate. The white precipitate was separated as a residual white solid via filtration and after washing with ethanol several times, e.g. three times. The residual white solid was dried under a reduced pressure and characterized by nuclear magnetic resonance (NMR), which showed that the residual white solid comprised pure dopamine sulfonate (DS). Full assignment of $^1H$ and $^{13}C$ spectra was obtained by 2D FT methods. A 3-{[2-(3,4-dihydroxyphenil)-ethyl]

amino}propane-1-sulfonic acid comprising: $^1$H NMR (800 MHz, $D_2O$): δ (ppm) 6.79 (d, J=8.1 Hz, 1H, H-5"), 6.74 (d, J=2.1 Hz, 1H, H-2"), 6.65 (dd, J=8.1, 2.1 Hz, 1H, H-6"), 3.19 (t, J=2×7.5 Hz, 2H, H-1'), 3.10 (m, 2H, H-3), 2.89 (t, J=2×7.4 Hz, 2H, H-1), 2.80 (t, J=2×7.4 Hz, 2H, H-2'), 2.01 (m, 2H, H-2). $^{13}$C NMR (201 MHz, $D_2O$): δ (ppm) 144.02 (C-3"), 142.85 (C-4"), 128.72 (C-1"), 120.90 (C-6"), 116.26 (C-2" and C-5"), 48.45 (C-1'), 47.58 (C-1), 45.93 (C-3), 30.75 (C-2'), 20.95 (C-2).

On a second synthesis step of step (iv), a zwitterionic dopamine sulfonate was obtained via preparing a dimethylformamide (DMF) solution comprising the dopamine sulfonate (0.3286 g, 1 mmol) by dissolving in 150 mL of DMF in a 500 mL round bottom flask. An anhydrous sodium carbonate (0.2544 g, 2.4 mmol) was added to the DMF solution, which partially dissolved in the DMF solution. Afterwards, the flask was evacuated and back-filled with N2 several times, e.g. three times, followed by an addition of iodomethane (2.2 mL, 35 mmol). The solution was stirred for 5-10 h at 50° C., which resulted in a complete dissolution of the sodium carbonate and consequently, the solution turned yellow upon completion of a methylation step. The DMF was removed using a rotary evaporator at 40° C. and an oily mixture was obtained. A mixture of DMF and ethyl acetate (1:10 v/v) was added to yield a pale-yellow crude product as a precipitate, which separated by filtration. Following the filtration, a DMF-acetone solution (1:10 v/v) was added to the crude product to obtain a mixture solution that was refluxed at 55° C. for 2 hrs. The mixture solution was further filtered and a remaining precipitate was collected. The described procedure was, i.e. reflux and filtration processes, repeated two more times, whereby a white solid powder was obtained and characterized by NMR, which showed the white solid to be a pure zwitterionic dopamine sulfonate (ZDS) with molecular structure as depicted in FIG. 5, comprising: $^1$H NMR (800 MHz, $D_2O$): δ (ppm) 6.79 (d, J=8.1 Hz, 1H, H-5"), 6.76 (d, J=2.1 Hz, 1H, H-2"), 6.68 (dd, J=8.1, 2.1 Hz, 1H, H-6"), 3.43 (m, 2H, H-1'), 3.42 (m, 2H, H-3), 3.06 (s, 6H, $N(CH_3)_2$, 2.92 (m, 2H, H-2'), 2.86 (t, J=2×7.2 Hz, 2H, H-1), 2.15 (m, 2H, H-2). $^{13}$C NMR (201 MHz, $D_2O$): δ (ppm) 144.02 (C-3"), 142.88 (C-4"), 128.02 (C-1"), 121.02 (C-6"), 116.40 (C-2"), 116.29 (C-5"), 64.42 (C-1'), 61.79 (C-3), 50.58 (t, $^1J_{C/N}$=3.5 Hz, $N(CH_3)_2$, 46.92 (C-1), 27.50 (C-2'), 17.95 (C-2).

Afterwards, the iron nanoparticles coated with silicon dioxide were coated with the water-soluble zwitterionic dopamine sulfonate (ZDS) as explained hereon.

A water-ethanol solution was prepared by mixing and stirring ethanol (100 ml) and purified water (10 ml) up to 250 rpm for few min. 25 mg of nanoparticles were dissolved in ethanol (2 ml) and added to the water-ethanol solution and stirred for half an hour. After that ZDS powder with ratio of 1:2 was added (50 mg) to obtain a precipitate comprising nanoparticles was collected by centrifugation and washed twice to remove excess of surfactants and/or reaction byproducts. The collected nanoparticles were kept in ethanol.

Furthermore, the synthesis explained above and depicted in FIG. 2 and FIG. 6, has been supported via a plurality of characterization method as explained hereon.

All chemicals unless indicated were obtained from Sigma Aldrich and used as received. Air-sensitive materials were handled in an Omni-Lab VAC glove box under a dry nitrogen atmosphere with oxygen levels lower than 0.2 ppm. All solvents were of spectrophotometric grade and purchased from EMD Biosciences. Transmission electron microscopy (TEM) images of iron oxide nanoparticles were obtained with a JEOL 200CX electron microscope operated at 200 kV. TEM samples were prepared by dropping a methanol solution containing a sample on a copper grid. Powder X-ray Diffraction (PXRD) measurements were performed with Panalytica. To estimate a crystal size of the nanoparticles, full-with-half-maximum (FWHM) peak fit for the (111) peak (with High Score Plus), and applied Sherrer formula where $$\text{crystallite (nm)} = \frac{K * \lambda}{\beta * \cos\theta}$$

where κ, λ, β and θ represents shape factor, X-ray wavelength, line broadening at half of maximum intensity and Bragg angle, respectively. Magnetic properties were characterized by using a Physical Properties Measurement System with a vibrating sample magnetometer (VSM) option. $^1$H and $^{13}$C NMR measurements were performed on Avance III NMR spectrometer (Bruker Biospin). Element analysis were carried out Spectra AA 220F flame atomic absorption spectrometer (Varian, Mulgrave, Australia) equipped with a deuterium lamp for background correction.

Below is Table 1 comprising data for synthesis of $Fe_2O_3$ nanoparticles, average nanoparticle size and nanoparticle shape. The nanoparticle shape and size were determined via TEM analysis. An example measurement is depicted in FIG. 7 with 3 sample: sample 1, sample 2 and sample 3.

TABLE 1

Synthesis of $Fe_2O_3$ nanoparticles

| Sample | PVP:$Fe(NO_3)_3$•$nH_2O$ [mol] | PVP (MW) | PVP concentration [g/ml] | Reaction condition | Shape | Core size [nm] |
|---|---|---|---|---|---|---|
| 1 | 1:50 | 40K | 0.34 | 2 h at 180° C. | Cube | 40 |
| 2 | 1:100 | 40K | 0.34 | 2 h at 160° C. | Cube | 25 |
| 3 | 1:6[1] | 40K | 0.34 | 2 h at 160° C. | Sphere | 14 |

Infrared spectroscopy (IR) measurements were made with an interferometer Vertex 80v Bruker FT/IR, with Glowbar (resistively heated SiC rod) as a light source and a Liquid Nitrogen cooling-Mercury Cadmium Telluride detector (LN-MCT). Measurements were made at room temperature (298 K), using 2 mm aperture and 0.5 $cm^{-1}$ resolution. IR spectra were acquired on a pressed pellet (diameter 3 mm) of a sample material mixed with pure and dry KBr powder. Such dilution was needed as the absorption lines were too strong. During the measurement, a sample was held in an evacuator at 1 hPa (E-3 atm) pressure compartment. IR spectra depicted in FIG. 5 shows successful coating of Fe@$SiO_2$ nanoparticles with ZDS. After modification, spectrum bonds S═O, C—N, C═C, C—H and OH stretching modes appear around 1300 $cm^{-1}$, 1350 $cm^{-1}$, 1690 $cm^{-1}$, 2950 $cm^{-1}$ and 3400 $cm^{-1}$, respectively. Si—O—Si stretching modes appear around 1080 $cm^{-1}$ represent $SiO_2$ coating.

FIG. 1 depicts a cubic shaped metal oxide nanoparticle according to embodiment of the present invention. In simple terms, to obtain the cubic shaped metal oxide nanoparticle, a method has been developed according to embodiments of the present invention, which comprise, but not limited to, varying a concentration of a reaction medium and a metal salt/size controlling agent stoichiometric ratio, for example iron salt/PVP as shown in Table 1.

In the prior art, synthesis of nanoparticles has been obtained by modifying PVP/Fe salts molar stoichiometric ratios, wherein nanoparticles were synthesized by thermal decomposition comprising using iron (II)pentacarbonyl and DMF. Decrease in particle size was observed when PVP concentration increased, and as a result, small spherical nanoparticles of about 8 nm in diameter were obtained. Furthermore, nanoparticles of controlled shape and size were obtained via carrying out a synthesis under nitrogen atmosphere, similar to as described in F. N. Sayed et al *Sci Rep* 5, 1-14, 2015.

However, in the present invention, the synthesis of nanoparticles may be done, for example, in an autoclave at a synthesis temperature between 160° C. and 180° C. for few hours. The synthesis temperature may also be referred to as reaction temperature. Furthermore, it may be possible to use different stoichiometric ratios of metal oxides and size controlling agent, for instance, of $Fe(NO_3)_3$*$nH_2O$) and PVP with molecular weight of 40000 g/mol, as shown in Table 1. As a result, an increase of the reaction temperature to 180° C. and decrease of iron concentration (1:50) may enable to obtain cubic-shaped nanoparticles with an edge length of approximately 40 nm, as depicted in FIG. 3. Further decrease of iron hydrate salts to PVP ratio it may yield smaller sphere-shape Nanoparticles with edge length of 14 nm compared to cubic shaped 25 nm at the same reaction conditions, as shown in Table 1 and depicted in FIG. 6. Therefore, embodiments of the present invention relate to the influence of temperature and precursor molecular concentration ratio on the size and shape of nanoparticles formation.

As depicted in FIG. 2, after the nanoparticle of iron oxide were synthesized, the first coating layer 104 was applying on the iron oxide nanoparticle using TEOS to form a $SiO_2$ layer. The coated iron oxide nanoparticle was collected a powder and subsequently mixed with $CaH_2$ and heated at approx. 300° C. for about 4 days in a vacuum-sealed Pyrex tube. $CaH_2$ is popular reduction agent and sensitive to air and moisture. Even though, a mechanism for reduction of metal oxides may be not exactly known, it may be that the actual reducing agent when using $CaH_2$ is metallic calcium, which may be produced by thermal decomposition as FIG. 6. Here, hydrogen gas may be formed and calcium cation may then penetrate the first coating layer 104, i.e. it may diffuse through $SiO_2$ pores present in the first coating layer 104, wherein the calcium cation may "grab" oxygen from the ferric oxide reducing the oxidation state of the ferric part to zero, i.e. to a metal state, and the calcium cation may form calcium oxide (CaO), which is known to be very a stable compound under the conditions described herein, which may be advantageous, as it may allow metal-based core nanoparticle to remain intact under vacuum.

In a further step, the reduced coated metal-based core nanoparticles 104' may be subjected to one or more washing steps comprising, for example, a washing procedure with a $NH_4Cl$/MeOH solution. In the present invention, the washing procedure has been proved an effective removal of by-products yielding reduced coated metal-based core nanoparticles 104' free of $CaH_2$ and/or CaO.

Furthermore, in the present example, the effective removal of $CaH_2$ and CaO has been confirmed via powder x-ray diffraction (PXRD) analysis, wherein spectral patterns corresponding to any calcium oxide peaks have been observed.

FIG. 7 depicts TEM images and FIG. 8 PXRD patterns, which were taken prior and posterior to the step (iii) depicted in FIG. 2, i.e. before and after the reduction. FIG. 8 depicts a PXRD revealing a hematite phase of the iron oxide with characteristic reflections at 24.1°, 33.2°, 35.6°, 40.8°, 49.5°, 54.1°, 62.5° and 64.0°. Moreover, it has been observed Miller indexes closely matching peak locations corresponding to hematite iron oxide phase. The nanoparticle described in the present example possesses a body-centred-cubic (bcc) crystal structure, which may indicate the coated metal-based core 104' comprises a pure metal-based core 102 a metal-based core 102 coated, which was confirmed via PXRD analysis as depicted in FIG. 11, wherein peaks indexed {110}, {200} and {211} are observed. Furthermore, as depicted in FIG. 3, it is possible to observe a color variation of the reaction mixture changing from orange-red (A) to black (B), which may indicate formation of metal iron ($Fe^0$).

Moreover, high resolution TEM analysis has confirmed formation of well-crystallized as depicted in FIG. 7. An increased of the edge length of the metal-based core 102 was observed after increased after the reduction step, wherein the edge length increased from approximately 25 nm to approximately 50 nm, as depicted in FIG. 7. Furthermore, TEM images in FIG. 7 show that the reduced particles, i.e. metal-based core 102, keep their original overall shape. A brighter core observed in FIG. 7 may be attributed to the removal of oxygen atoms during the reduction step.

Furthermore, magnetic properties of coated metal-based core 104' were measured at room temperature using a VSM option of the physical properties measurement system (PPMS, Quantum Design). The coated metal-based core 104' were analyzed as powder samples in the field range of −1.5 to 1.5 Tat 300 K.

FIG. 12 depicts the saturation magnetization ($M_s$) of the coated metal-based core 104' to be 124 emu per g-Fe. This $M_s$ value is smaller than that of bulk α-Fe, which is 218 emu per g-Fe. Such a variation of the $M_s$ may indicate that the metal-based core 102 may have undergo slightly oxidized, which may be attributed to the porosity of the first coating layer 104, i.e. the $SiO_2$ shell may not completely be oxygen-tight due to the presence of micropores. However, the coated metal-based core 104' remain substantially metallic, i.e. with an oxidization number of zero. The coated metal-based core 104' are of ferromagnetic origin and exhibit a coercivity ($H_c$) of 0.019 T.

The nanoparticle 100 described in the present invention may also encounter applications, for instance, in biomedical fields. For this reason, embodiments of the present invention comprise a step (iv) wherein the coated metal-based core nanoparticle 104' may be covered by a subsequently coating. In other words, the surface of the coated metal-based core nanoparticle 104' may be modified with a second coating layer 106 to obtain a double-coated metal-based coating 106'. Such an approach may be advantageous, as it may allow to supply to the nanoparticle 100 a layer, e.g. a layer comprising an organic ligand such as a zwitterionic dopamine sulfonate (ZDS), which may increase the solubility of the nanoparticle 100 in a given solvent, for instance, in water.

FIG. 5 depicts IR analysis wherein a successful synthesis of a double-coated metal-based core nanoparticle 106' is achieved, i.e. a successful synthesis of cubic iron-based core 102 coated with a first coating layer 104 and a second coating layer 106. Additional toxicological profile is explained herein.

Example 2: Cubic Iron Core-Shell Nanoparticles Functionalized to Obtain High-Performance MRI Contrast Agents FIG. 10 schematically depicts a plurality of steps (i), (ii), (iii) and (iv) of a second example, wherein a cubic iron core-shell nanoparticle was functionalized to obtain a high-performance magnetic resonance imaging contrast agent via a synthesis method explained hereon.

FIG. 10 (i) depicts a first step (i), wherein monodispersed cubic ferric oxide ($Fe_2O_3$) nanoparticles were synthesized via a one-step solvothermal route from a reaction mixture of ferric nitrite ($Fe(NO_3)_3$ $nH_2O$; 99.9%, Sigma-Aldrich), N,N-dimethyl formamide (DMF; 99.8%, Sigma-Aldrich) and poly pyrrolidone (PVP, Fluka). The reaction mixture was stirred for 30 minutes and sealed in an autoclave. The reaction mixture was heat-controlled up to 200° C. for 4 days. Subsequently, the reaction mixture was cooled down to room temperature, followed by a plurality of washing steps, e.g. three washing cycles with ethanol. As a result, nanoparticles with cubic structure with an approximately edge length of 40 nm were obtained. The nanoparticles with said formed may also be referred to as nanocubes.

FIG. 10 (ii) depicts a second step (ii), wherein a cubic hematite $SiO_2$-coated ($Fe_2O_3@SiO_2$) nanoparticle was synthesized via coating the nanoparticles with a silane-based layer using tetraethyl orthosilicate (TEOS, 98%, Sigma-Aldrich), where 1 ml of TEOS was added to 30 ml ethanol solution and stirred for 1 hour. The ferric oxide nanoparticles (109 mg/g) in ethanol solution were mixed with ethanol-water solution (1:10), to which 2.5 ml of ammonium hydroxide ($NH_3OH$, 28%, Sigma-Aldrich Chemical Co) was added. The reaction mixture was sealed, stirred and continuously sonicated at room temperature for one hour. TEOS-ethanol was added to the reaction mixture containing the metal oxide-based nanoparticles over the course of 8 hours. The nanoparticles were extracting from the reaction mixture using a magnet and subsequently washed with ethanol and dried in air to obtain a powder comprising the metal oxide-based nanoparticle coated with a silane-based first coating layer.

FIG. 10 (iii) depicts a third step (iii), wherein the coated iron oxide nanoparticle was subjected to a $CaH_2$ reduction reaction to obtain cubic $Fe@SiO_2$ nanoparticles. For this purpose, a reduction reaction was carried out using $CaH_2$ as a reducing agent. However, it should be understood that plurality of other reducing agents be utilized. The reduction reaction with $CaH_2$ executed for the present invention comprises a weight excess and a reaction temperature according to embodiments of the present invention. The ferric oxide nanoparticle coated with the first coating layer was finely ground with three weight excess of $CaH_2$ (99.6%, Sigma-Aldrich Chemical Co) under Argon atmosphere in a glove box, sealed in an evacuated Pyrex tube and heated at up to 300° C. for 4 days. By-products, such as CaO and residual $CaH_2$, were removed from the reaction mixture by washing the reaction mixture with a $NH_4Cl$/methanol (99.9%, Fluka) solution under air atmosphere.

TRXF measurements were performed to determine iron content in the $SiO_2$ coated nanoparticles. Determining iron content in the nanoparticle may be important to obtain a saturation magnetization value in units of emu per g-Fe. It should be understood that similar determination may be performed for other metal-based nanoparticles, e.g. emu per g-Co for a nanoparticle comprising a cobalt-based core, emu per g-Ni for a nanoparticle comprising a nickel-based core. The saturation magnetization as obtained from Physical Property Measurement System (Quantum Design PPMS-14T) was divided by the mass of pure iron in the sample. The latter was determined by TRXF and atomic absorption spectroscopy with both being commonly used methods giving very similar results. In order to estimate the amount of iron in the iron-based nanoparticles coated with a first coating layer ($\alpha$-$Fe@SiO_2$ nanocubes). A nanoparticle suspension was mixed 1:1 with gallium internal standard and 5 μl of the as-prepared mixture was pipetted onto a quartz carrier disc (Bruker). The concentration of iron was quantified with Spectra software (AXS Microanalysis GmbH). Iron content in the cubic $\alpha$-$Fe@SiO_2$ nanocubes sample was measured to be 33% wt. For comparison, iron content in spherical nanoparticles (maghemite ($\gamma$-$Fe_2O_3@SiO_2$)) was also checked, comprising an iron concentration of 27% wt.

Furthermore, a Spectra AA 220F flame atomic absorption spectrometer (Varian, Mulgrave, Australia) equipped with deuterium lamp for background correction was used. Acetylene of 99.99% purity (AGA, Helsinki, Finland) was used as fuel gas. Iron was extracted from the samples with concentrated nitric and hydrofluoric acids (1 ml of the mixture 1:1) in a water bath at 85° C. for 120 min. After cooling down the samples were diluted to 100 mL with Milli-Q water. Iron content in the cubic nanoparticles ($\alpha$-$Fe@SiO_2$) was 33% wt. For comparison, iron content in spherical nanoparticles (maghemite ($\gamma$-$Fe_2O_3@SiO_2$)) was also checked, comprising an iron concentration of 27% wt.

FIG. 10 (iv) depicts a fourth step (iv), wherein the iron nanoparticle coated with a first siloxane layer was subsequently coated with 3-aminopropyltrimethoxysilane ($NH_2$-silane). For this purpose, silane coating was carried out using 3-aminopropyltrimethoxysilane ($NH_2$-silane), (97%, Sigma-Aldrich) to obtain iron-based core coated with a first coating layer comprising a silane layer and a second coating layer comprising an amino silane layer ($Fe@SiO_2@NH_2$-silane). 1 mL of amino silane was added to 30 mL ethanol solution and stirred for 1 hour. The metal-based nanoparticle coated with the first coating layer ($Fe@SiO_2$) in ethanol were mixed with an ethanol-water solution ratio (1:10), followed by the addition of 2.5 ml of $NH_3OH$ (28%, Sigma-Aldrich) and stirred for one hour. Subsequently, silane-ethanol solution was added to the $Fe@SiO_2$ nanoparticle during 8 hours, while stirring and sonicating the mixture.

IR measurements were performed with an interferometer Vertex 80v Bruker FT/IR, with Glowbar (resistively heated SiC rod) as a light source and a Liquid Nitrogen cooling-Mercury Cadmium Telluride detector (LN-MCT). Measurements were made at room temperature (298 K), using 2 mm aperture and 0.5 cm-1 resolution. IR spectra were acquired on a pressed (60 MPa pressure) pellet (diameter 3 mm) of a sample material mixed with pure and dry KBr powder (Spectra shown in ESI). Such a dilution carried out as consequence of strong absorption lines. During the measurement, the sample was in evacuator till 1 hPa ($E^{-3}$ atm) pressure compartment.

Powder x-ray diffraction measurements were carried out using Panalytic Powder 3 with Cu $K_\alpha$ radiation ($\lambda$=0,154 nm) beam voltage of 30 kV and beam current of 40 mA. Patterns were collected in a range of 20° to 90° with the step of 0.02° and the exposure time of 2 sec. TEM (JEOL JEM-1400) low and high-magnification observation was used to characterize obtained nanocubes morphology. TEM specimens were prepared by dropping a nanoparticle solution on a copper grid and air dried. A Physical Property Measurement System (Quantum Design PPMS-14T) with a vibrating sample magnetometer (VSM) attachment was used to study the magnetic properties of the nanoparticles. IR spectra were collected on Bruker FT/IR. The samples were mixed with KBr and compressed into pellets. Furthermore, the nanoparticles samples were scanned by clinical whole-body MRI system Achieva 3.0T, Philips, The Netherlands. Relaxivity $r_2$ was calculated from signal intensities acquired by multi-echo TSE sequence with the following parameters: repetition time TR=2000 ms, echo train length ETL=8, echo time TE=10 to 80 ms with increment 10 ms, flip angle FA=90 deg, FOV=160 mm, image matrix 512×512, slice thickness 5 mm, number of excitations NEX=2.

Described below are experimental details, which for sake of clarity have been limited to a brief explanation. Monodispersed cubic $\alpha$-$Fe_2O_3$ Nanoparticles were synthesized by a facile one-step solvothermal route from ferric nitrite [$Fe(NO_3)_3$*$nH_2O$], N,N-dimethyl formamide (DMF) and poly pyrrolidone and heated up to 180° C. for several hours. The crystallographic structure of the obtained nanoparticles was confirmed by powder X-ray diffraction (PXRD) analysis, shown in FIG. 11 *a*. The PXRD pattern revealed the hematite phase of iron oxide with characteristic reflections at 24.1°, 33.2°, 35.6°, 40.8°, 49.5°, 54.1°, 62.5° and 64.0° with the Miller indexes closest matching peak locations of hematite iron oxide phase PDF card 033-0664 from the ICDD PDF-2 database. The cubic shape with the cube's edge of 40 nm on average was evident from transmission electron microscope (TEM) analysis (FIG. 11*c*). The nanoparticles were next coated with an $SiO_2$ layer. As depicted in FIG. 11*c*, TEM images confirm an average $SiO_2$-coating thickness of 10 nm on average.

Subsequently, the cubic $\alpha$-$Fe_2O_3$@$SiO_2$ nanoparticles were subject to reduction with $CaH_2$ to obtain $SiO_2$-coated cubic $\alpha$-Fe@$SiO_2$ Nanoparticles (FIG. 11 *d*). The mixture of nanoparticles and $CaH_2$ was heated at 300° C. for few days. The color of the reaction mixture changed from orange-red to black, indicating the formation of metal iron $Fe^0$. The structure of the pure metallic body-centered-cubic (bcc) $\alpha$-Fe core was confirmed by PXRD analysis (FIG. 11 *b*) with {110}, {200} and {211} peaks indexed. TEM images in FIG. 11 *d* reveal voids in the reduced Nanoparticles due to oxygen leaving the iron oxide Nanoparticles upon reduction. Therefore, the morphology of the as-synthesized nanoparticles could be referred to as quasi- or pseudo-cubic.

Nanoparticles' magnetic properties were characterized with PPMS (Quantum Design) magnetometry after exposure to air for 7 days. FIG. 15 depicts a magnetic hysteresis curve of a magnetic measurement of $\alpha$-Fe@$SiO_2$. The $M_s$ value observed for the nanoparticles is 181 emu per g-Fe. The obtained saturation magnetization is nearly twice as large as for commercially available contrast agents, e.g. a commercial SPION contrast agent Resovist, which exhibit a saturation magnetization of about 95 emu per g-Fe, and close to that of bulk iron, which exhibits a saturation magnetization of about 218 emu per g-Fe as disclosed in D. L. Huber et al *Small* 1 428-501, 2005.

The mass fraction of cubic $\alpha$-Fe in the $SiO_2$-coated nanoparticles was found to be 33% by using total reflection X-ray fluorescence spectroscopy (TRXF) Picofox S2 and elemental analysis. The mass fraction value was used to calculate the mass of iron in the nanoparticles for MRI measurements. The mass fraction of iron for spherical maghemite (γ-Fe2O3@SiO2) was found to be 27% using the same methods.

The surface of the $SiO_2$ coated iron nanoparticles was further modified with a 3-aminopropyltriethoxysilane ($NH_2$-silane) for additional coating with functional molecules, such as albumin. Moreover, an $NH_2$-silane coating is useful since it can make the nanoparticles dispersible in aqueous solutions over a wide pH range, link to biomolecules, including applications, such as, but not limited to, in DNA and RNA purification, and enhance cellular uptake of nanoparticles without an increased cytotoxicity. The $NH_2$-silane coating was successfully implemented as confirmed with Fourier transform infrared (FTIR) spectroscopy, as depicted in FIG. 13.

Figure 14:
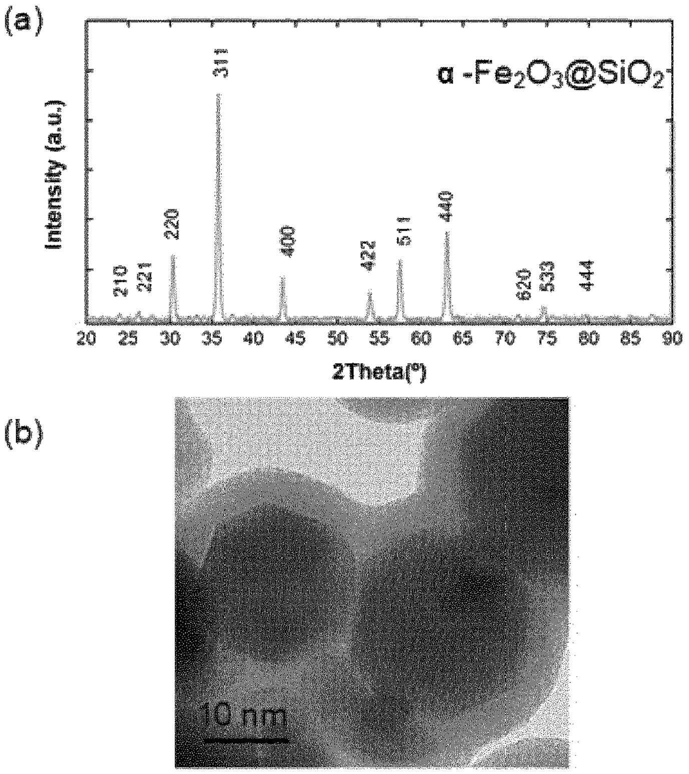

The transverse relaxivity ($r_2$) of the as-synthesized cubic $\alpha$-Fe@$SiO_2$ Nanoparticles was tested with a clinical 3.0 T Philips Achieve MRI scanner. As reference compounds, commercially available spherical maghemite coated with $SiO_2$ ($\gamma$-$Fe_2O_3$@$SiO_2$) was used, the latter structure is confirmed by PXRD analysis as depicted in FIG. 14 *a*. $SiO_2$-coating was implemented by the same procedure as described above.

FIG. 14 *b* depicts TEM images of $\gamma$-$Fe_2O_3$@$SiO_2$ nanoparticles with a core diameter of 60 nm. FIG. 15 depicts obtained $r_2$ values were 55 $s^{-1}$ $mM^{-1}$ for spherical $\gamma$-$Fe_2O_3$@$SiO_2$, and 109 $s^{-1}$ $mM^{-1}$ for cubic $\alpha$-Fe@$SiO_2$, which indicates that pure metal $\alpha$-Fe@$SiO_2$ nanoparticles have nearly twice as high $r_2$ relaxivity compared to maghemite $\gamma$-$Fe_2O_3$@$SiO_2$ nanoparticles. This can be attributed to the larger $M_s$ values of pure metal nanoparticles. In the information available in the prior art, $r_2$ values of iron oxides magnetite and maghemite may vary according to particle size and the size of the polymer shell. In general, larger nanoparticles have enhanced $r_2$ relaxivity and depending on the prior art, the values for spherical SPIONs range from as little as 13 $s^{-1}$ $mM^{-1}$ to 385 $s^{-1}$ $mM^{-1}$. However, in the present invention, $\alpha$-Fe nanoparticles showed clearly enhanced MRI relaxivity compared to maghemite nanoparticles.

Dynamic light scattering studies revealed the average hydrodynamic size (Dh) of nanoparticles to be between 100-200 nm for $\alpha$-$Fe_2O_3$ and $\alpha$-$Fe_2O_3$@$SiO_2$, 200-400 nm for $\alpha$-Fe@$SiO_2$ and 600-800 nm for $\alpha$-Fe@$SiO_2$@$NH_2$-silane in Milli Q (MQ) water. Dh of nanoparticles was larger than the primary core with the $SiO_2$ shell size determined by TEM. The polydispersity index (PDI) of Nanoparticles was between 0.07 and 0.31, showing the monodispersity and stability of NP solutions.

Hereafter an example of nanoparticles as contrast agents are explained. As an application example iron nanocubes coated with silica oxide and zwitterion as dual MRI contrast agents are detailed.

For this purpose, MRI in vivo experiment in a rat was performed. Rats at 8 months (n=6, WT; n=6, KO) and 15 months of age (n=6, WT; n=7, KO) were anaesthetized using isoflurane (1.5-2.5% in 1.51/min medical oxygen) and placed on a heated animal bed throughout the MRI procedure. All scans were performed using a 9.4T Bruker BioSpec 94/20 USR system connected to a 1H circular polarized transceiver coil and running ParaVision 6.0.1® software (Bruker BioSpin Group, Bruker Corporations, Germany). Respiration and temperature were monitored using a respiration pillow and a rectal probe (SA Instruments Inc., Stony Brook, USA). Respiration rate was maintained at between 35-70 breaths per minute. Two orientation pilot scans were performed in order to establish the position of the animal and identify anatomical landmarks relevant for planning the subsequent scan. The final T1 and T2-weighted sequence was performed using the following parameters: repetition time (TR) 6 (100, 200, 400, 800, 1600 3200) ms, echo time (TE) 10 ms to 160 ms, flip angle 90 degrees, number of averages 5, imaging matrix 320×192 or 256×256.

A volume of Fe@$SiO_2$ nanoparticles (400 μL) with nanoparticles size of 15 nm and 40 nm in a physiological solution (BBraun NaCl 0.9%) with a concentration of 200 mg/L were injected to the tale vein. After 10-30 minutes T1 and T2 scans were carried out and compared with pre-injected body scans and after injection to rat tale vein with Fe@$SiO_2$ and Fe@$SiO_2$@ZDS in a physiological solution as depicted in FIGS. 16A, 16B, 17C, 17D, 18 and 19, helping to image rats' organs such as kidneys, liver stomach and brain. Furthermore, time dependence in FIG. 19 before and after 5 min and 30 min nanoparticles injections shows the stomach, kidneys and liver becoming visually sharper.

TABLE 2 nanoparticles with different shape and coating characterized measured using 2% agarose gel on 9.4 T MRI.

| Contrast agent (CA) | $r_1$ ($L^*mmol^{-1}s^{-1}$) | $r_2$ ($L^*mmol^{-1}s^{-1}$) |
|---|---|---|
| A | 0.154 | 44.88 |
| B | 0.0735 | 22.89 |
| C | 0.1993 | 34.14 |
| D | 0.0348 | 16.27 |

$$R1 = \frac{1}{\Delta T1 + c[mM]}$$

$$R2 = \frac{1}{\Delta T2 + c[mM]}$$

where, R1 and R2 may be plotted against different magnetic particles concentrations in vials. Least-squares linear fit can be completed among the points where the slope value may be used as an estimate for r1 and r2, following a similar approach as described in M. Rohrer et al Investigative Radiology, 40, 715-724, 2005.

While in the above, a preferred embodiment has been described with reference to the accompanying drawings, the skilled person will understand that this embodiment was provided for illustrative purpose only and should by no means be construed to limit the scope of the present invention, which is defined by the claims.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

The invention claimed is:

1. A nanoparticle comprising:

a metal-based core, a first coating layer substantially covering the metal-based core to generate a coated metal-based core, and a second coating layer at least partially covering the coated metal-based core, wherein the metal-based core comprises at least one transition metal, and wherein the metal-based core comprises the at least one transition metal substantially in a state of zero oxidation, wherein the first coating layer comprises a siloxane-based layer as represented in Formula 1:

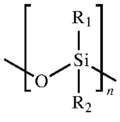

wherein in Formula 1 n is an integer greater than or equal to 1 and less than or equal to 15, and $R_1$ and $R_2$ are each a moiety that is independently selected from a group consisting of —CHO, —COH, —COOH, —SH, —$CONH_2$, —$PO_3H$, —$OPO_4H$, —$SO_3H$, —$OSO_3H$, —$N_3$, —OH, —SS-, —H, —$NO_2$, —CHO, —COOCO—, —CONH—, —CN, —$NH_2$, —RHO, —ROH, —RCOOH, —RNH, —$NR_3OH$ wherein R is $C_nH_{2n}$ wherein n is an integer greater than 0 and less than or equal to 15, and —COX wherein X is one of F, Cl, Br, and I; and wherein the second coating layer comprises zwitterionic dopamine sulfonate (ZDS).

2. The nanoparticle according to claim 1, wherein the at least one transition metal comprises at least one transition metal selected from a group consisting of Fe, Co, and Ni.

3. The nanoparticle according to claim 1, wherein:

the first coating layer comprises an inner terminal portion and an outer terminal portion, wherein the inner terminal portion defines an inner surface and the outer terminal portion defines an outer surface of the first coating layer, and the second coating layer comprises an inner terminal portion and an outer terminal portion, wherein the inner terminal portion defines an inner surface and the outer terminal portion defines an outer surface of the second coating layer.

4. The nanoparticle according to claim 1, wherein the nanoparticle comprises a cubic crystal structure, wherein the crystal structure comprises an edge length between 1 and 100 nm.

5. The nanoparticle according to claim 1, wherein the nanoparticle exhibits at least one of:

a saturation magnetization ($M_s$) in the range of 40 to 218 emu per g-M, and a coercivity ($H_c$) lower than 0.050 T.

6. The nanoparticle according to claim 1, wherein the nanoparticle is water soluble and exhibits a polydispersity index (PDI) lower than 0.7.

7. The nanoparticle according to claim 1, wherein the nanoparticle is suitable for magnetic resonance imaging.

* * * * *